United States Patent [19]

Calderon et al.

[11] Patent Number: 4,738,979
[45] Date of Patent: Apr. 19, 1988

[54] α₂-BLOCKING DERIVATIVES OF IMIDAZOLE

[75] Inventors: Piedad Calderon, Brussels; Alexis A. Cordi, Chaumont-Gistoux; Claude L. Gillet, Blanmont; Hugo J. Gorissen, Grez-Doiceau; Georges E. Lambelin, Brussels; Joseph L. Roba, Dion Valmont; Michel P. Snyers, Limal; William R. van Dorsser, Court-St-Etienne, all of Belgium

[73] Assignee: G. D. Searle & Co., Chicago, Ill.

[21] Appl. No.: 823,157

[22] Filed: Jan. 27, 1986

[30] Foreign Application Priority Data

Jan. 28, 1985 [LU] Luxembourg .................. 85747

[51] Int. Cl.⁴ ............... A61K 31/415; C07D 233/64; C07D 233/58
[52] U.S. Cl. ................... 514/396; 514/400; 548/335; 548/342
[58] Field of Search ............... 548/335, 342; 514/396, 514/400

[56] References Cited

U.S. PATENT DOCUMENTS 4,605,661 8/1986 Hirsch et al. .............. 548/335 X

Primary Examiner—Richard A. Schwartz
Attorney, Agent, or Firm—J. Timothy Keane; Paul D. Matukaitis

[57] ABSTRACT

A compound of the formula:

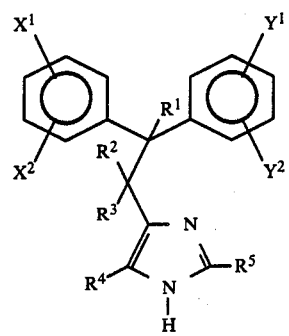

wherein $X^1$, $X^2$, $Y^1$ and $Y^2$, whether or not identical are hydrogen, a halogen such as fluoro, chloro or bromo, linear or branched alkyl of 1 to 3 carbon atoms, linear or branched alkoxy of 1 to 3 carbon atoms, carboxy, alkoxy-carbonyl of 1 to 3 carbon atoms or phenyl;
$R^1$ is hydrogen, methyl or phenyl;
$R^2$ and $R^3$, which may or may not be identical, are hydrogen, hydroxyl, linear or branched alkyl of 1 to 6 carbon atoms, or linear or branched alkoxy group of 1 to 4 carbon atoms;
$R^1$ and $R^2$ may together form a carbon-carbon double bond; and
$R^4$ and $R^5$ whether or not identical, are hydrogen, linear or branched alkyl or 1 to 3 carbon atoms.

The compounds are useful as blocking agents of α₂-adrenergic receptors.

78 Claims, No Drawings

$\alpha_2$-BLOCKING DERIVATIVES OF IMIDAZOLE

The present invention relates to derivatives of imidazole and to their salts of addition with pharmaceutically utilisable acids, the processes for their preparation and pharmaceutical compositions containing at least one of these derivatives or its salt of addition, and their utilisation as blocking agents of $\alpha_2$-adrenergic receptors and as agents possessing an anti-convulsive activity.

$\alpha$-adrenergic receptors are subdivided into $\alpha_1$ and $\alpha_2$ receptors essentially on the basis of their response to specific antagonistic agents, and it has been found that $\alpha_2$ receptors are located at the level of the noradrenergic nerve endings where they are involved in the "release" of noradrenaline, and that there exist $\alpha_2$ receptors which are present in various tissues as for example in the pancreas, the blood platelets, the adipose tissues, the blood vessels.

In view of their biological activities, selective $\alpha_2$ receptor blocking agents are of great interest for the therapeutic treatment of depressive illness and of cerebral ageing, such as senile dementia, some cardiac deficiencies and asthma, and for the prophylactic and curative treatment of ailments in which platelet hyperaggregability is involved, such as migraine and thrombotic ailments.

Further said compounds are of value for the treatment of metabolic troubles such as diabetes and obesity, of sexual inadequacies, of certain forms of hypertension and as anorexigenic and diuretic agents. Although the existence of $\alpha_2$-adrenergic receptors was described several years ago, at present very few compounds possessing selective $\alpha_2$-blocking activity are known. The agents most described and most cited in literature are yohimbine and rauwolscine, but these products lack selectivity and possess numerous side-effects which prevent their use as therapeutics. The other products described in recent literature are experimental compounds of which little is known as regards their therapeutic potential. Among these compounds there are derivatives of imidazoline such as those described in British Pat. No. 2,068,376, British Patent Application No. 2,102,422 A and EP No. 0092,328.

In this class of derivatives, 2-[2-(1,4-benzodioxanyl)]-2-imidazoline hydrochloride (Idazoxan hydrochloride) seems to be the compound of greatest interest.

Another class of compounds is that containing an imidazole group, especially 2-[2-(1,4-benzodioxanyl)alkyl]-imidazoles, described by L. M. Caroon et al. [J. Med. Chem., 25, 666–670 (1982)] and 4-(phenylalkyl)imidazoles, 4-(phenylalkanoyl) imidazoles and 4-[(phenyl)-hydroxyalkyl]-imidazoles described in European patent application EP No. 0,034,473.

The present invention involves imidazole compounds and pharmacologically acceptable, nontoxic salts thereof, their process of preparation, pharmaceutical compositions containing such compounds, and therapeutic methods of use of such compounds.

The compounds of the present invention have the general formula I:

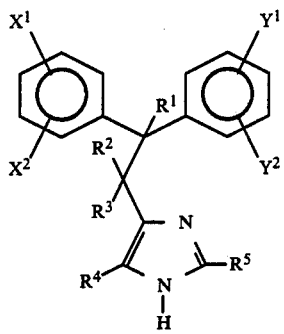

wherein:
$X^1$, $X^2$, $Y^1$ and $Y^2$, which may or may not be identical, are selected from the group consisting of hydrogen, a halogen such as fluoro, chloro and bromo, a linear or branched alkyl radical having from 1 to 3 carbon atoms, a linear or branched alkoxy radical having from 1 to 3 carbon atoms, carboxy, alkoxy, carbonyl having from 1 to 3 carbon atoms, and phenyl;

$R^1$ is selected from the group consisting of hydrogen, methyl and phenyl;

$R^2$ and $R^3$, which may or may not be identical, are selected from the group consisting of hydrogen, hydroxyl, linear or branched alkyl having from 1 to 6 carbon atoms, and linear or branched alkoxy having from 1 to 4 carbon atoms;

$R^1$ and $R^2$ may together form a carbon-carbon bond, which signifies that the carbon atoms $R^1$ and $R^2$ can be connected by a double bond, as represented below:

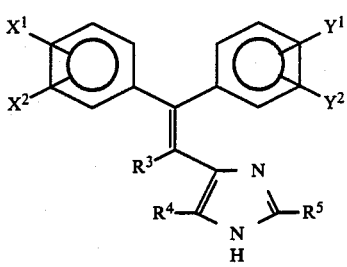

$R^4$ and $R^5$, which may or may not be identical, are hydrogen or a linear or branched alkyl radical having from 1 to 3 carbon atoms, also the corresponding geometric isomers, in the pure form or in the form of a mixture, and the corresponding optically pure isomers, racemic or non-racemic mixtures of these isomers, the various possible tautomers, and the salts of addition of these compounds formed with pharmaceutically utilizable acids.

A preferred class of the compounds corresponding to the general formula I is that in which: $X^1$, $X^2$, $Y^1$ and $Y^2$, which may or may not be identical, are hydrogen, a fluoro or chloro group, methyl, methoxy or phenyl radical;

$R^1$ is hydrogen or a methyl group;

$R^2$ is hydrogen, a hydroxyl, methyl or methoxy group;

$R^1$ and $R^2$ may together form a carbon-carbon double bond;

$R^3$ is hydrogen or a linear or branched alkyl group having from 1 to 4 carbon atoms;

$R^4$ and $R^5$, which may or may not be identical, are hydrogen or methyl.

Another preferred class of compounds corresponding to the general formula I is that in which: $X^1$, $X^2$, $Y^1$ and $Y^2$, which may or may not be identical, are hydrogen, a fluoro or chloro, methyl, methoxy or phenyl radical; $R^1$, $R^2$, $R^3$, $R^4$ and $R^5$ are hydrogen; and $R^1$ and $R^2$ may together form a carbon-carbon double bond.

Another class of compounds of formula I consists of those compounds wherein $X^1$, $X^2$, $Y^1$ and $Y^2$ are different from hydrogen. Those compounds wherein each of $X^2$ and $Y^1$ is hydrogen are suitable. Still another class of compounds consists of those compounds wherein each of $X^1$, $X^2$, $Y^1$ and $Y^2$ is hydrogen. Another class of compounds is wherein one or both of $X^1$ and $Y^1$ are fluoro. Another class of compounds consists of those compounds wherein each of $R^1$, $R^2$, $R^4$ and $R^5$ is hydrogen.

Another preferred class of compounds corresponding to the general formula I is that in which:

$X^1$, $X^2$, $Y^1$, $Y^2$, $R^1$, $R^4$ and $R^5$ are hydrogen;

$R^2$ is hydrogen or a linear or branched alkoxy radical having from 1 to 3 carbon atoms;

$R^3$ is hydrogen or a linear or branched alkyl radical having from 1 to 3 carbon atoms; and $R^1$ and $R^2$ together form a carbon-carbon double bond.

Examples of compounds according to the invention are: 4(5)-(2,2-diphenyl ethyl)imidazole,
4(5)-[(2,2-diphenyl-1-methyl)ethenyl]imidazole,
4(5)-{[2-(3-methylphenyl)-2-phenyl]ethyl}imidazole,
4(5)-{[2-(2-chlorophenyl)-2-phenyl]ethyl}imidazole,
4(5)-{[2-(4-fluorophenyl)-2-phenyl]ethyl}imidazole,
4(5)-{[2-(2-fluorophenyl)-2-(4'-fluorophenyl)]ethyl}imidazole,
4(5)-{[2-(4-methoxyphenyl)-2-phenyl]ethyl}imidazole,
4(5)-[(2,2-diphenyl-1-n.propyl)ethenyl]imidazole,
4(5)-[2-(1,1-diphenyl)-pentyl]imidazole,
4(5)-[2-(1,1-diphenyl-2-methoxy)pentyl]imidazole,
4(5)-(2,2-diphenylethyl)-2-methylimidazole,
4(5)-(2,2-diphenylethyl)-5(4)-methylimidazole.
4(5)-{[2-(2-fluorophenyl)-2-(6'-fluorophenyl)]ethyl}imidazole,
4(5)-{[2-(2-fluorophenyl)-2-phenyl]ethyl}imidazole,
4(5)-{[2-(4-biphenyl)-2-phenyl]ethyl}imidazole,
4(5)-[1-(2,2-diphenyl)-propyl]imidazole,
4(5)-{[2-(2-methylphenyl)-2-(5'-methylphenyl)]ethyl}imidazole
4(5)-{[2-(2-methylphenyl)-2-(4'-methylphenyl)]ethyl}imidazole.

The products according to the invention may likewise be present in the form of a salt of addition with a pharmaceutically utilisable acid, such as an inorganic acid such as hydrochloric acid, sulphuric acid or phosphoric acid, or an appropriate organic acid such as an aliphatic, cycloaliphatic, aromatic, araliphatic or heterocyclic, carboxylic or sulphonic acid, such as formic, acetic, propionic, succinic, glycolic, gluconic, lactic, malic, tartaric, citric, ascorbic, glucuronic, maleic, fumaric, pyruvic, aspartic, glutamic, benzoic, anthranilic, hydroxybenzoic, salicylic, phenylacetic, mandelic, embonic, methanesulphonic, ethanesulphonic, pantothenic, toluenesulphonic, sulphanilic, cyclohexylaminosulphonic, stearic, alginic, β-hydroxybutyric, malonic, galactaric, galacturonic acid.

If the derivatives of formula I are present in the form of salts of addition with acids, they can be transformed according to usual processes into free bases or into salts of addition with other acids. The compounds of formula I in which $R^1$ and $R^2$ together represent a carbon-carbon bond can be present in the form of cis-trans geometric isomers, or in the form of pure isomers, or in the form of a mixture in equal or unequal proportions.

The compounds of formula I can possess one or more asymmetric carbon atoms and are thus capable of existing in the form of optical, racemic or diastereo isomers; all these forms are part of the present invention The products according to the invention comprising one or more centres of asymmetry can be utilised either in the form of mixtures containing several diastereo isomers, whatever are the relative proportions thereof, or in the form of pure diastereo isomers.

Furthermore the pairs of enantiomers can be present in equal proportions (racemic mixtures) or unequal proportions.

Finally the product can be utilised in the form of an optically pure compound.

The optical isomers can be obtained by resolution of the racemic compounds according to conventional processes, for example by formation of diastereoisomer salts by treatment with optically active acids, such as tartaric, diacetyltartaric, tartranilic, dibenzoyltartaric, ditoluoyltartaric acid, and separation of the mixture of diastereo isomers, for example by crystallisation or chromatography, followed by liberation of the optically active bases from these salts.

The optically active compounds according to formula I can likewise be obtained by utilising optically active starting products.

The present invention also covers pharmaceutical compositions containing, as active ingredient, at least one compound of the general formula I or its salt of addition with a pharmaceutically utilisable acid, in the presence or absence of an excipient.

These compositions are prepared in such manner that they can be administered by oral, rectal, parenteral or local route.

They can be solids, liquids or gels and be presented, according to the administration route, in the form of powders, tablets, lozenges, coated tablets, capsules, granulates, syrups, suspensions, emulsions, solutions, suppositories or gels. These compositions can likewise include another therapeutic agent having an activity similar to or different from that of the products of the invention.

In order to facilitate administration, these pharmaceutical compositions can be presented in the form of unit doses.

The products according to the invention are in general endowed with selective $\alpha_2$-blocking properties.

Consequently, as indicated, these products can be utilized in the treatment of depressive and degenerative diseases of the central nervous system. In addition, the products can be utilized as anti-migraine, antithrombotic, antiasthmatic, diuretic, anorexigenic and antidiabetic agents and for the treatment of certain forms of hypertension, obesity, certain cardiac diseases or sexual inadequacies.

Certain compounds according to the invention also possess pharmacological activity involving the central nervous system, for example an anticonvulsive activity, whether or not associated with an effect on $\alpha$-adrenergic receptors. Such compounds can be utilized in the treatment of various forms of epilepsy and dyskinesia.

Some compounds have also been observed to block biogenic amines uptake by rat synaptosomes, which emphasizes their utility as anti-depressants.

Certain compounds according to the invention possess $\alpha_2$-agonist properties which render them of interest for the treatment of gastroduodenal ulcers and certain forms of hypertension.

The compounds according to the invention are prepared according to several processes which are part of the present invention and are described below. In the case where these processes give rise to the production of new intermediate compounds, these as well as the processes serving for their preparation likewise form part of the present invention.

1. According to a first process, the compounds of formula I are obtained by synthesis of the imidazole group from an appropriate starting product.

Several methods are known for carrying out the synthesis of the imidazole group, as described e.g. by H. Bredereck et al. [Angewandte Chemie, 71, 759–764 (1959)] and by M. R. Grimmett [Advances in Heterocyclic Chemistry, Ed. A. R. Katritzky and A. J. Boulton, Academic Press, Vol. 12, 104–137 (1970) and Vol. 27, 242–269 (1980)].

Some of these methods are indicated below by way of non-limitative examples.

1.1. According to a first procedure, the compounds of formula I are obtained by condensation of a carbonyl derivative of formula IIa and IIb, the carbonyl group of which may be latent, for example in the form of an acetal or thiocetal, whether or not cyclic, with a nitrogenous reagent III, followed if appropriate by a complementary conversion according to Diagram 1.1. below.

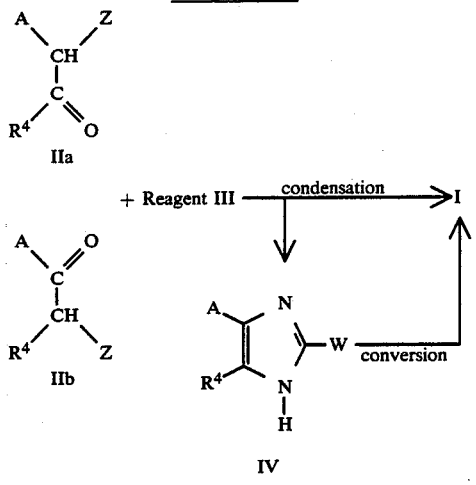

Diagram 1.1.

In this diagram, A represents the group

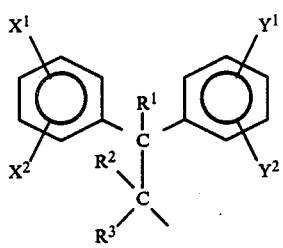

$X^1$, $X^2$, $Y^1$, $Y^2$ and $R^1$ to $R^4$ having the values defined above, Z represents a function such as a hydroxy radical, an oxoradical, an atom of halogen, an amino group, an alkanoyloxy radical, W represents a substituent which is easily eliminated, for example by hydrolysis, hydrogenation, desulphurisation, hydrogenolysis, diazotisation or oxidation, such as a mercapto or amino group, and the reagent III represents a nitrogenous compound or a combination of two compounds at least one of which is nitrogenous, as for example an amide of formula $R^5$—$CONH_2$, an amidine of formula

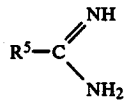

or an iminoether of formula

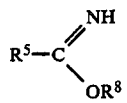

in the presence or absence of ammonia, cyanamide, guanidine, an alkaline or ammonium thiocyanate, or formaldehyde in the presence of ammonia.

In the above formulae $R^5$ possesses the values defined previously and $R^8$ is an alkyl group $C_1$-$C_3$.

Hereinafter the symbols A, Z, W and $R^1$ to $R^8$ are as defined above, unless otherwise indicated. The choice of the reagent III and of the experimental conditions take place according to the nature of the group Z of the molecule IIa or IIb.

Thus in the case where Z represents an atom of halogen or an oxo-, hydroxyl, alkanoyloxy or amino radical, the synthesis of a compound of formula I is effected by condensation of the compound IIa or IIb with an amide of formula $R^5$—$CONH_2$ which is often likewise used as solvent, at an elevated temperature which may reach the reflux temperature, under an inert atmosphere or advantageously under an atmosphere of ammonia.

A very practical variant of this process consists in preparing the $\alpha$-halocarbonyl derivative of formula IIa or IIb (Z=halogen) in situ, for example by bromination of a carbonyl derivative of formula Va or Vb,

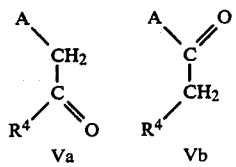

in formamide, followed by its condensation with formamide by heating of the reaction medium. Another useful procedure consists in generating an $\alpha$-amino-carbonyl derivative of formula IIa or IIb (Z=$NH_2$) in situ, by catalytic reduction in formamide or acetamide, of an oxime of formula VIa or VIb,

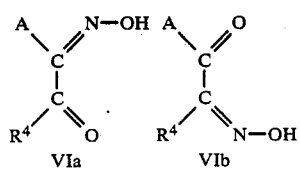

which can easily be obtained for example by conversion of a carbonyl derivative of formula Va or Vb into a nitroso compound according to known methods.

The use of an amide $R^5\text{-CONH}_2$ as reagent III gives very good results in the case where $R^5$ represents hydrogen or a methyl radical.

The variant of the process utilising an amidine

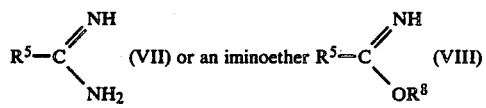

as reagent enables one to obtain derivatives of formula I in which $R^5$ represents either an atom of hydrogen or an alkyl radical having from 1 to 3 carbon atoms $C_1$-$C_3$, in good yield.

In the usual way, the amidine and the iminoether are used in the form of salts of addition with an acid, for example in the form of hydrochloride or acetate.

The condensation proceeds easily by mixing the reagents IIa or IIb and VII or VIII in a suitable solvent such as an alcohol, in the presence of ammonia and/or a strong base such for example as an alcoholate of an alkaline, the reaction medium advantageously being heated. Another way to transform an α-aminocarbonyl derivative of formula IIa or IIb (Z=NH$_2$) into a compound of formula I consists in the condensation of the compound IIa or IIb with a potassium thiocyanate followed by the complementary conversion of the intermediate IV (W=SH) formed (cf. Diagram 1.1.). The condensation is effected easily by heating a mixture of the two reagents in a solvent such as water and the intermediate IV (W=SH) is then converted into a derivative of formula I, for example by oxidation.

This can be done for example by treating the intermediate IV in aqueous medium with nitric acid at a moderate temperature.

1.2. The imidazole nucleus can likewise be formed from an alkene of formula IX $$A\text{---}CH\text{=}CH\text{---}R^4 \quad \quad \quad IX.$$

The alkene IX is transformed into a derivative of formula I by treatment with nitrosonium tetrafluoroborate in the presence of a nitrile of formula $R^5$—CN utilised likewise as solvent, followed by a complementary conversion of the intermediate X with the aid of titanium trichloride, in accordance with Diagram 1.2.a.

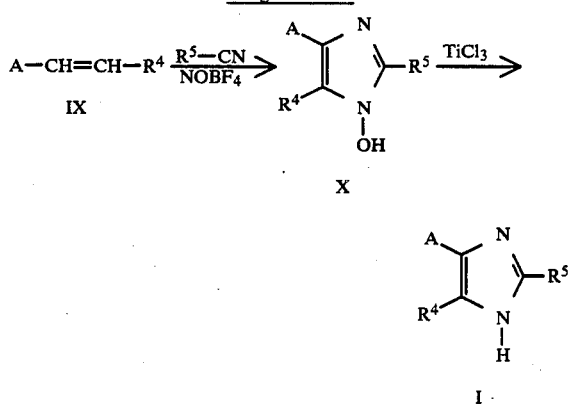

An alkene of formula IX can likewise be used to obtain a derivative of formula I, as indicated in Diagram 1.2.b.

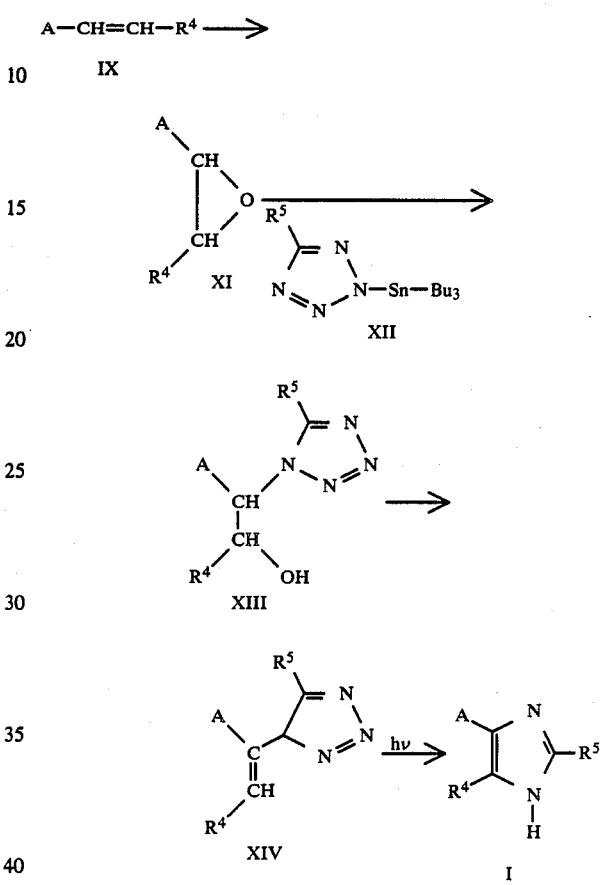

The alkene IX is converted by conventional methods into an epoxide of formula XI which is condensed with a tri-n.butylstannyl tetrazole of formula XII, obtained from a nitrile $R^5$—CN and tri-n.butyl tin azide, by reacting the reagents XI and XII in an inert solvent such as diethyl ether, at room temperature, followed by a treatment with gaseous hydrochloric acid.

The alcohol XIII obtained is dehydrated in vinyl tetrazole XIV, for example by means of triphenoxyphosphonium iodide in N,N-dimethyl formamide at room temperature, this dehydration being followed by a treatment by an alkaline hydroxide in aqueous solution.

The irradiation, advantageously at 254 nm, of the intermediate XIV in an appropriate solvent such as an alcohol or a hydrocarbon optionally in the presence of an acid as catalyst, supplies the compound I in good yield.

1.3. Another way of synthesizing the imidazole group can be carried out starting from a heterocyclic group. Thus the compounds of formula I are obtained starting from an imidazoline of formula XV in accordance with Diagram 1.3.a.

Diagram 1.3.a.

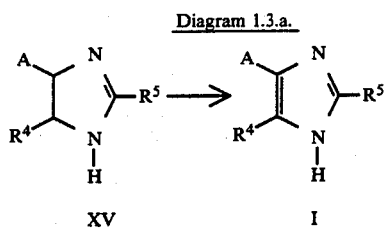

The transformation of the imidazoline XV is effected either by means of an appropriate oxidising reagent, such for example as manganese dioxide in an inert solvent such as acetone, at moderate temperature, or by dehydrogenation, carried out at elevated temperature (>150° C.) in an inert solvent with the aid of an appropriate catalyst, such as a catalyst based upon nickel, platinum or palladium and optionally in the presence of a co-reagent such as copper oxide or sulphur.

Starting from an oxazole of formula XVI, the compounds of formula I are easily obtained according to Diagram 1.3.b. by heating the oxazole XVI in the presence of ammonia or advantageously in the presence of formamide.

Diagram 1.3.b.

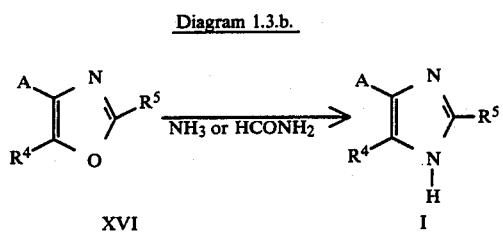

1.4. Another way of synthesising the imidazole group consists of condensing an enamine of formula XVII with an amidine VII or with an N-chloro-amidine XVIII in accordance with Diagram 1.4..

Diagram 1.4.

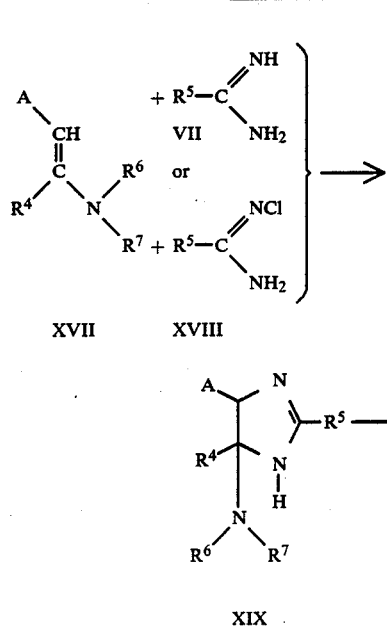

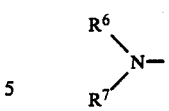

represents the amino group of the enamine, such for example as a dialkylamino or morpholino group.

The condensation takes place under an inert atmosphere, under anhydrous conditions, in the case of an amidine in the presence of an equimolar quantity of bromine, in an inert solvent such as dichloromethane and advantageously in the presence of an organic base such as triethylamine or pyridine.

The intermediate aminoimidazoline XIX is deaminated into a derivative of formula I, either already in situ under the utilised reaction conditions, or by heating the intermediate XIX in the presence of triethylamine hydrochloride or pyridine hydrochloride.

1.5. A last method mentioned below for the synthesis of the derivatives of formula I ($R_4=R_5=$hydrogen) by formation of the imidazole group consists of the condensation of a nitrile XX or of an aldimine XXI with an isonitrile of formula XXII, in accordance with Diagram 1.5.

Diagram 1.5.

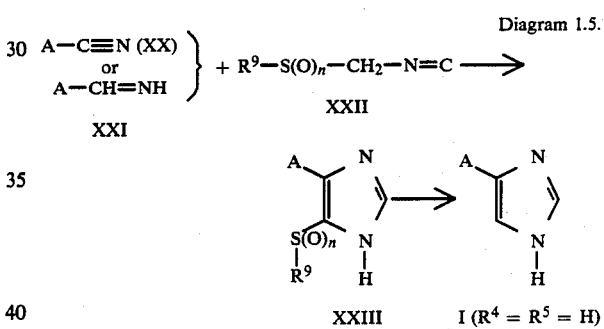

In this diagram, A possesses the value defined above, n is equal to 0 or 2 (condensation with a nitrile XX) or n is equal to 0 (condensation with an aldimine XXI) and $R^9$ represents a methyl or tolyl group.

The condensation is effected under anhydrous conditions by opposing the reagents in an inert solvent such as tetrahydrofuran (THF) at room temperature in the presence of a strong base, as for example potassium tert.butoxide; a consecutive treatment with water furnishes the intermediate XXIII. If the nitrile XX is subject to steric hindrance the condensation is most advantageously effected by reacting this nitrile with the anion of XXII generated by means of butyl lithium in anhydrous THF at low temperature. The intermediate XXIII is converted into a compound of formula I ($R^4=R^5=$hydrogen), for example by desulphurisation by means of hydrogen in the presence of Raney nickel.

2. According to a second process, the compounds according to the invention are obtained by grafting of the imidazole group onto a suitable substrate.

2.1. A first procedure, illustrated by Diagram 2.1., consists in substituting the group L of a compound of formula XXIV by an imidazole group, in general utilised in the form of an organolithiated derivative of formula XXV.

Diagram 2.1.

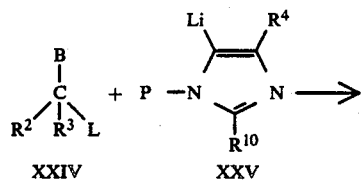

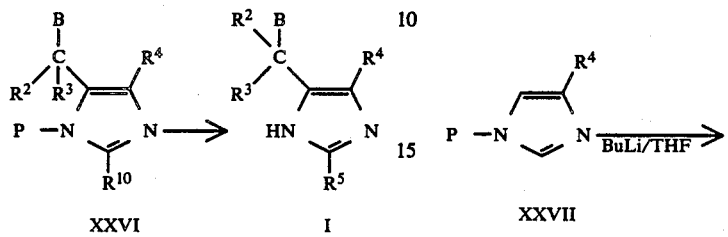

In this diagram B represents the group

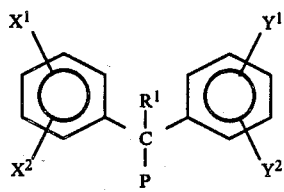

L is an easily substitutable radical such as a halogen like chlorine, bromine, iodine, an O-tosyl group or an O-mesyl group.

P represents a protective group such for example as an alkyloxymethyl, benzyloxymethyl, dialkoxymethyl, trimethylsilylmethyl, [2-(trimethylsilyl)ethoxy]methyl, trityl, vinyl, benzyl, N,N-dialkylaminosulphonyl, 2-chloroethyl, 2-phenylsulphonylethyl, diphenyl methyl or [(bistrifluoromethyl) (4-chlorophenoxymethoxy)]methyl radical, $R^{10}$ represents the group $R^5$ or a group substitutable by hydrogen, such for example as a phenylthio or alkylthio group.

Hereinafter the radicals $X^1$, $X^2$, $Y^1$, $Y^2$, $R^1$ to $R^{10}$, B, L and P are as defined previously, unless otherwise indicated.

The organolithium derivative XXV is prepared by lithiation of an N-protected imidazole and substituted in the 2 position by a group $R^{10}$, provided that $R^{10}$ does not represent hydrogen, by means of n-butyl lithium at low temperature, under an inert atmosphere and in an inert solvent such as diethyl ether or THF.

The substitution of the L group of the substrate XXIV proceeds by addition of this compound at low temperature, in solution in an appropriate solvent such as THF, anhydrous diethyl ether or a saturated hydrocarbon, to the solution of the lithiated reagent XXV.

After reaction the mixture is brought to room temperature, treated by a protic solvent such as water, and acidified to supply either the desired derivative of formula I directly or the intermediate of formula XXVI which by deprotection is converted into a compound of formula I.

The protection of the imidazole group in the 2 position by a phenylthio or alkylthio group is effected by lithiation of an N-protected imidazole, followed by a reaction with an alkyl disulphide or a phenyl disulphide under conditions similar to those described for the substitution of the imidazole group in the 4 position. The same procedure can be utilised for the introduction of the group $R^5$, $R^5$ being an alkyl radical $C_1$-$C_3$, into an imidazole of formula XXVII, utilising a reagent of formula $R^5$ L in which $R^5$ is an alkyl radical $C_1$-$C_3$, according to the following diagram, L and P being defined above.

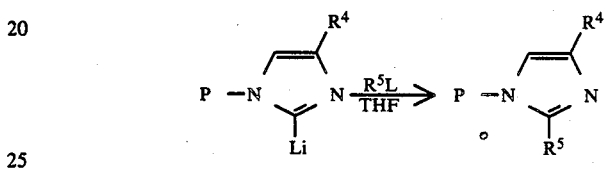

Of course the above-stated procedure can likewise be utilised for the conversion of a derivative of formula I in which $R^5$ represents hydrogen into a derivative of formula I in which $R^5$ represents an alkyl group $C_1$-$C_3$ according to the following diagram:

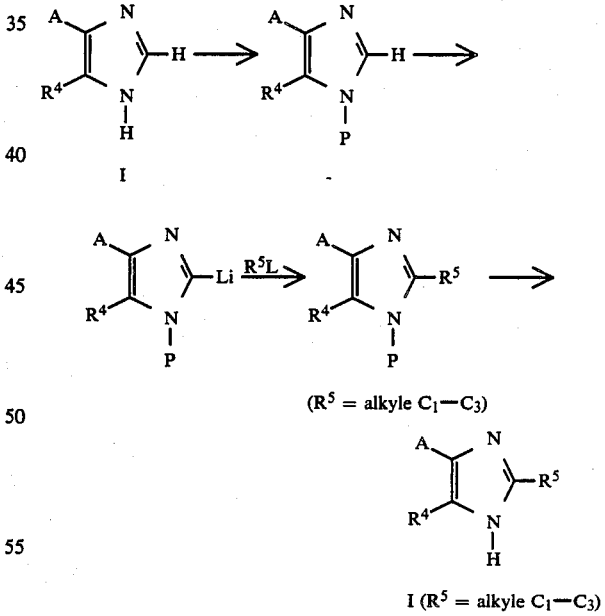

The protection of the nitrogen of the imidazole group is effected according to known methods, for example by treatment of the imidazole XXVIII in the presence of a base in a solvent such for example as dimethyl formamide or 1,2-dichloroethane in the presence of a phase transfer catalyst, with a reagent of formula P L (XXIX), P and L being defined above, according to the diagram:

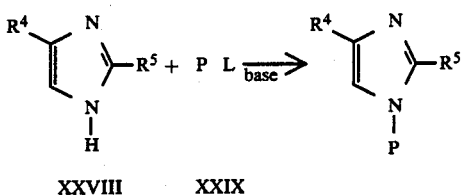

XXVIII    XXIX

The deprotection of the imidazole group is effected by known methods:

the radical $R^{10}$, being an alkylthio or phenylthio group, is substituted by hydrogen, for example, by a desulphurisation by means of hydrogen at elevated temperature in the presence of a catalyst such as Raney nickel, the radical P is substituted by hydrogen by different methods selected as a function of the nature of P, such for example as:

(a) by acidolysis in aqueous or non-aqueous medium by means of an acid such as a halogenated hydracid, acetic acid, trifluoroacetic acid, sulphuric acid, at a temperature which can vary from room temperature to reflux temperature, (b) by treatment with tetra-n.butylammonium fluoride in THF at room temperature, (c) by treatment with sodium hydride in dimethyl formamide at room temperature, followed by hydrolysis, (d) by catalytic hydrogenation (hydrogenolysis), (e) by treatment with sodium hydride, followed by hydrolysis and reaction at elevated temperature with sodium acetate in acetonitrile.

2.2. According to a second procedure, the derivatives of formula I are obtained by condensation of an organolithiated derivative XXV with a carbonyl derivative of formula XXX or XXXI followed by a deprotection and possibly a complementary conversion, in accordance with Diagram 2.2.

Diagram 2.2.

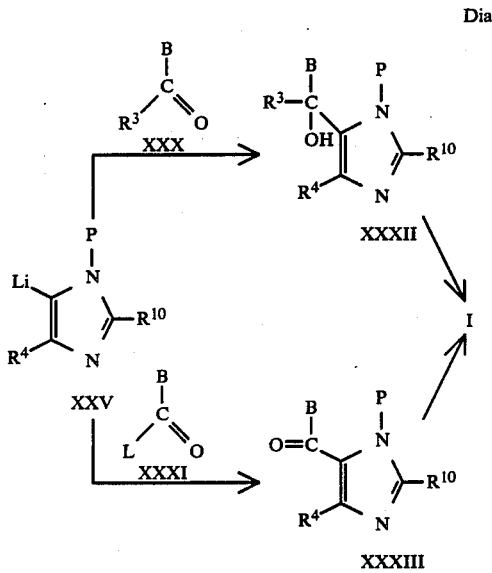

The experimental conditions of the condensation and the deprotection are the same as those described in paragraph 2.1. Any complementary conversion to obtain a derivative of formula I from the intermediates XXXII and XXXIII can be effected in one or more steps, from deprotected, partially deprotected or protected intermediates, according to conventional methods selected as a function of the nature of the intermediate and of the compound I to be obtained, as for example:

(a) by dehydration of XXXII (this method is of particular interest for obtaining a derivative of formula I in which $R_1$ and $R_2$ together represent a carboncarbon bond, possibly followed by a hydrogenation of the alkene of formula I into another compound of formula I ($R_1$ and $R_2$=hydrogen), (b) by alkylation, for example by means of a reagent of formula $(R^{11}O)_2SO_2$ or $R^{11}X$ wherein $R^{11}$ represents a linear or branched alkyl radical $C_1$-$C_4$ and X possesses the values defined above (easy method for the preparation of derivatives of formula I in which $R^2$ represents an alkoxy group $C_1$-$C_4$), (c) by substitution of the hydroxyl radical by a halogen, such as chlorine or bromine, by means of an halogenating agent such as $PBr_5$ or $SOCl_2$, and conversion of this alkyl halide by hydrogenolysis, alkylation or by dehydrohalogenation into a compound of formula I, (d) by hydrogenolysis, (e) by reduction of an intermediate of formula XXXII or XXXIII, (f) by alkylation of a derivative of formula XXXIII by the expedient of an organometallic derivative, such as an organomagnesium compound of formula $R^{12}MgX$ or an organolithium compound of formula $R^{12}Li$, $R^{12}$ being a linear or branched alkyl radical $C_1$-$C_6$, followed if necessary by one or more of the above conversions in order to obtain the desired derivative of formula I.

2.3 According to a variant of this process, the derivatives of formula I are likewise obtained by photochemical addition of an imidazole derivative XXVIII, optionally in its form protected by the radicals $R^{10}$ and/or P defined above, to a carbonyl derivative of formula XXX, followed if appropriate by a complementary conversion and/or a deprotection in order to obtain a compound of formula I, according to Diagram 2.3.

Diagram 2.3.

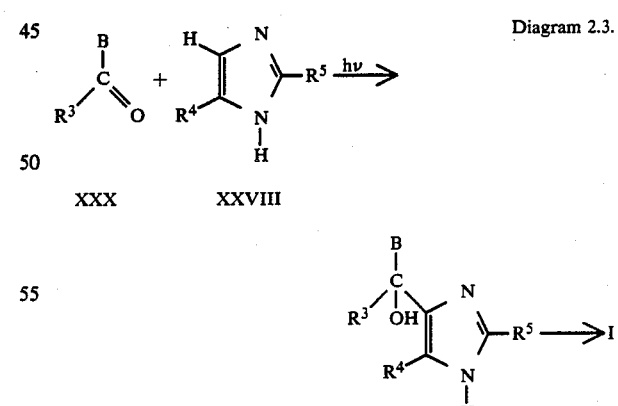

B, $R^3$, $R^4$ and $R^5$ possess the values defined above. The addition is produced by irradiation under inert atmosphere either of a solution of the reagents in an inert solvent such as acetonitrile, or of a mixture of the reagents at room temperature or in gaseous phase.

The complementary conversion and the deprotection take place as described above.

3. According to a third procedure, the derivatives of formula I are obtained by coupling of two suitable reagents by effecting a carbon-carbon bond.

3.1. According to a first method, the carbon-carbon bond is realised by condensation of an organometallic derivative XXXIV with a halogenated or carbonyl derivative XXXV, such as a ketone, an aldehyde, an ester or an acid halide, according to Diagram 3.1. below.

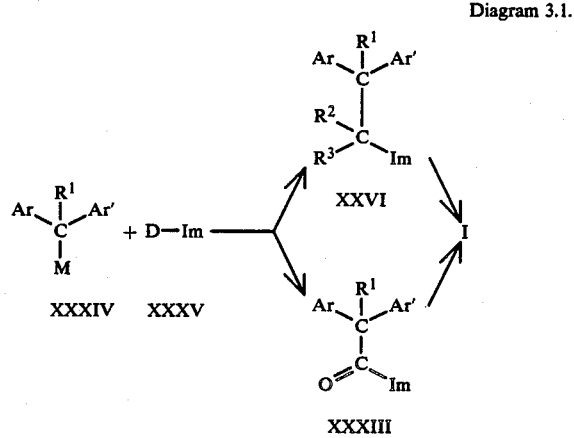

Diagram 3.1.

In this diagram:

M represents an atom of a metal such as lithium, sodium or potassium or a radical containing a metal such as magnesium, as for example MgCl or MgBr, zinc, copper or titanium.

D represents a halogenated or carbonyl group such as

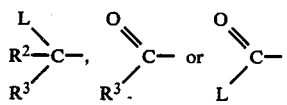

wherein

L represents an atom of chlorine, bromine or iodine,
Im represents the imidazole group of formula

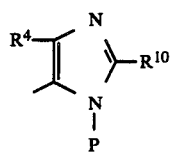

protected by a radical P in the 1-position and a radical $R^{10}$ in the 2-position in which P and $R^{10}$ possess the values defined above, Ar represents the group

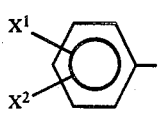

Ar' represents the group

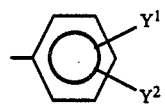

and $X^1$, $X^2$, $Y^1$, $Y^2$, $R^1$ to $R^{10}$ possess the values defined above.

The preparation of the organometallic derivative XXXIV is effected in conventional manner, either by transmetallation, or by acid-base reaction of the compound (Ar) (Ar') ($R^1$) C—H with a strong base such for example as butyl lithium or sodium amide.

The condensation is effected by reacting XXXIV and XXXV under experimental conditions similar to those stated above in process 2 for the condensation of an organolithiated derivative with a halogenated or carbonyl derivative.

3.2. A variant of this process consists in obtaining the carbon-carbon bond by condensation of an organometallic derivative of formula XXXVI with a halogenated or carbonyl derivative of formula XXXVII and converting the intermediate XXVI, XXXVIII and XXXIX into a compound of formula I, in accordance with diagram 3.2. below.

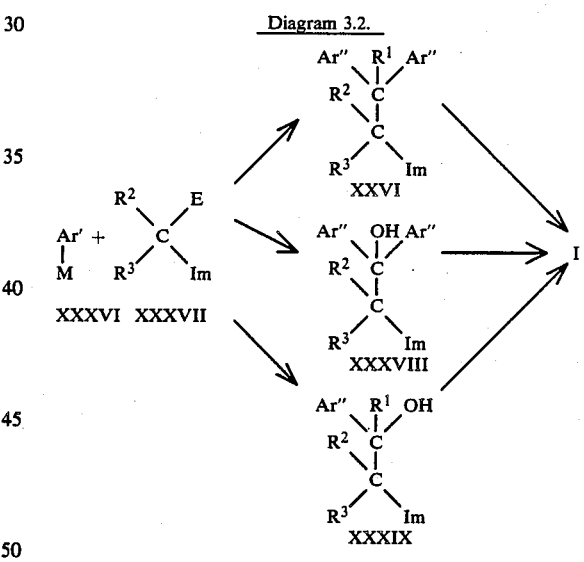

Diagram 3.2.

In this diagram, E represents a halogenated and/or carbonyl group of formula

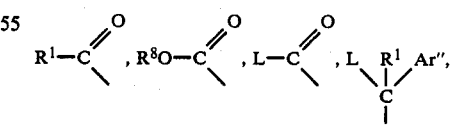

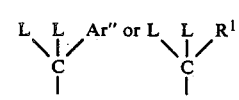

Ar" represents a group Ar or Ar' as defined above and M, L, Im and $R^1$ to $R^{10}$ represents the above-stated values.

The preparation of the organometallic derivative XXXVI and its condensation with compound XXXVII are effected in accordance with known methods similar to those described above for processes 2 and 3.

3.3. Another variant of the process consists in obtaining the coupling of the reagents by effecting the carbon-carbon bond by condensation of two carbonyl derivatives in the presence of titanium as catalyst, followed by the conversion of the intermediate, in accordance with diagram 3.3..

Diagram 3.3.

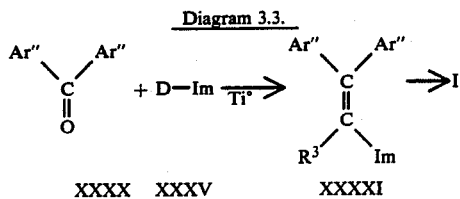

XXXX  XXXV           XXXXI

In this diagram, D represents the group

and Ar″, $R^3$ and Im possess the values defined above. The condensation of the carbonyl derivatives is effected in accordance with a known method by heating these derivatives in an inert solvent such as dimethoxyethane in the presence of activated titanium, obtained by reaction of metallic lithium with titanium trichloride in an inert solvent.

3.4. Another variant of the above coupling consists in effecting the carbon-carbon bond by condensation of a carbonyl derivative of formula XXXX with a phosphorus ylide of formula XXXXII followed by the conversion of the intermediate XXXXI into a derivative of formula I, according to diagram 3.4.

Diagram 3.4.

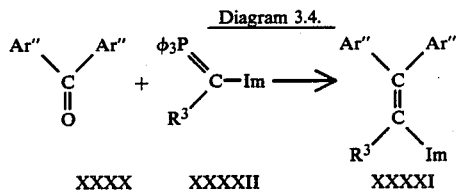

XXXX      XXXXII       XXXXI

Ar″, Im and $R^3$ possess the values already defined and $\phi$ represents the phenyl group.

The condensation of the carbonyl derivative with the phosphorus ylide is effected under anhydrous conditions, optionally with slight heating, by reacting the reagents in dimethyl sulphoxide, followed by hydrolysis of the reaction medium. The ylide itself is obtained by treating the corresponding alkyltriphenylphosphonium halide with a strong base such as sodium hydride in anhydrous dimethyl sulphoxide.

3.5. The functional groups in each of diagrams 3.1., 3.2., 3.3. and 3.4. are interchangeable and and these process variants, which are effected under the same experimental conditions as those described above, are technically equivalent to the methods 3.1., 3.2., 3.3. and 3.4.

By way of illustration such a variant is represented in diagram 3.5.

Diagram 3.5.

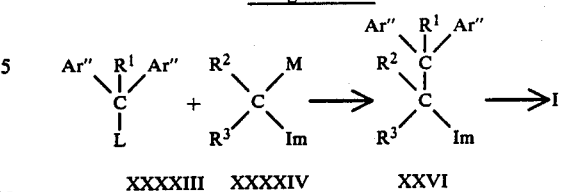

XXXXIII   XXXXIV        XXVI

In this diagram, Ar″, L, M, Im and $R^1$ to $R^3$ possess the values defined above.

The deprotection of the imidazole group and, if appropriate, the complementary conversion of the obtained intermediate, protected or not at the level of the imidazole group, likewise take place by the same reactions as those already described for processes 1 and 2, especially by dehydration, hydrogenation, reduction, alkylation, arylation or halogenation followed by alkylation, arylation or dehydrohalogenation.

The derivatives and the reagents utilised for this process are either commercially available or easily obtained by conventional methods from available starting materials. Thus for example derivative XXXVII

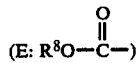

is obtained from a 4(5)-(alkoxycarbonylmethyl) imidazole by bromination followed by an alkylation according to the following diagram:

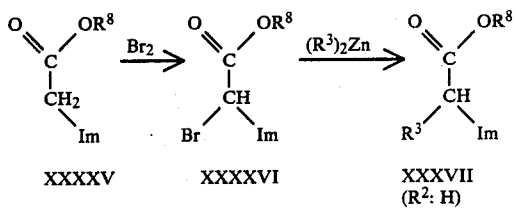

XXXXV         XXXXVI         XXXVII
                             ($R^2$: H)

The compound of formula XXXVII

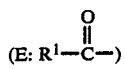

is obtained for example from a suitable alkyl halide by metallation followed by a reaction with an alkanoyl halide according to the following diagram:

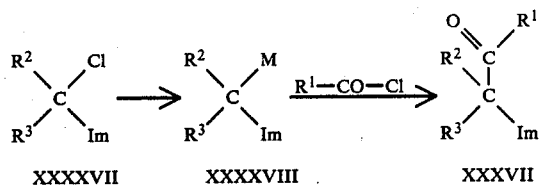

XXXXVII        XXXXVIII         XXXVII

In the above diagrams the symbols $R^1$ to $R^8$, M and Im represent the same values as those defined above.

The selection of the process for preparation of derivatives of formula I, of the reagents and of the experimental conditions is effected in such manner as to keep intact the part of the substrate which does not participate in the envisaged transformation or conversion.

Some detailed examples of preparation of the derivatives according to the invention are given below with the purpose of non-limitatively illustrating the particular characteristics of the processes according to the invention.

EXAMPLE 1

Synthesis of 4(5)-(2,2-diphenylethyl)-5(4)-methyl imidazole 5.

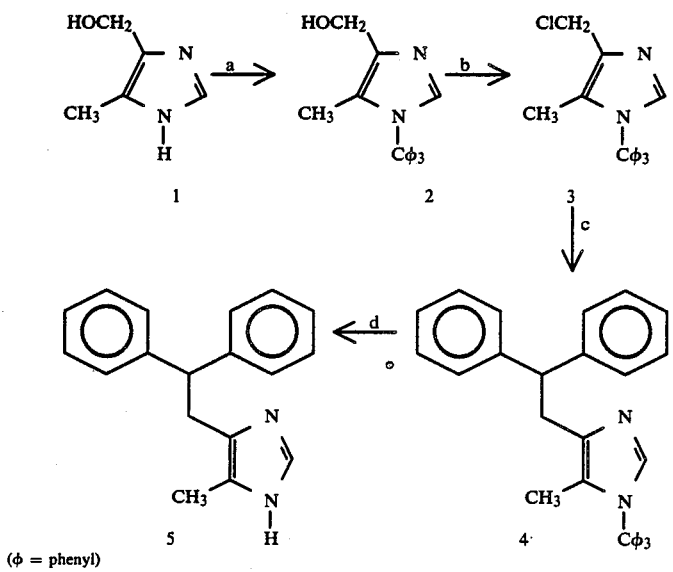

(φ = phenyl)

a. Synthesis of 1-trityl-4-hydroxymethyl-5-methylimidazole 2.

71.6 g of chlorotriphenylmethane are added, progressively and under nitrogen, to a solution of 12.5 g of 4(5)-hydroxymethyl-5(4)-methylimidazole 1 and 75 ml of triethylamine in 150 ml of anhydrous DMF, previously cooled (ice bath). At the end of the addition the reaction mixture is stirred for 16 hours at room temperature. It is then poured into 1.2 l of water and extracted with chloroform. The organic phase is washed with water, dried over magnesium sulphate and evaporated under reduced pressure. The residue is dispersed in 1 l of ether and cooled (ice bath), 1-trityl-4-hydroxymethyl-5-methylimidazole 2 crystallizes in the form of a white solid which is filtered and washed successively with hot isopropanol and ether.

M.p. 231°14 232° C.

b. Synthesis of 1-trityl-4-chloromethyl-5-methylimidazole 3.

0.41 ml of thionyl chloride are added drop by drop to a solution of 2 g of 1-trityl-4-hydroxymethyl-5-methylimidazole 2 and 0.83 ml of triethylamine in 28 ml of anhydrous benzene. After 45 minutes of stirring at room temperature the solution is filtered and the precipitate is washed with benzene.

The combined organic phases are dried over calcium chloride and evaporated under reduced pressure. Thus 1-trityl-4-chloromethyl-5-methylimidazole 3 is obtained in the form of a yellow solid which is immediately used in the following step.

c. Synthesis of 1-trityl-4-(2,2-diphenylethyl)-5-methylimidazole 4.

22.5 ml of a 0.5M solution of the lithiated derivative of diphenylmethane in THF are added drop by drop to a suspension of 0.5 g of cuprous cyanide (CuCN) in 10 ml of anhydrous THF cooled to −78° C. (solid carbon dioxide, acetone). At the end of the addition the reaction mixture is allowed to warm up to room temperature for some minutes.

Then it is cooled again to −78° C. and a solution of 1-trityl-4-chloromethyl-5-methylimidazole 3 in 10 ml of anhydrous THF is added thereto. After stirring for an hour at −78° C. the reaction mixture is kept at −20° C. for 48 hours. Then 30 ml of an aqueous 10% ammonia solution saturated with ammonium chloride are added and the mixture is extracted with ether. The organic phase is washed with water, dried over potassium carbonate and evaporated under reduced pressure. The residual oil is dispersed in heptane and cooled with an ice bath. This causes the precipitation of a yellow solid which is recrystallised in isopropanol. The 1-trityl-4-(2,2-diphenyl ethyl)-5-methylimidazole 4 is so obtained in the form of a white solid.

M.p. 205°–206° C.

d. Synthesis of 4(5)-(2,2-diphenyl ethyl)-5(4)-methylimidazole 5.

A solution of 0.83 g of 1-trityl-4(2,2-diphenylethyl)-5-methylimidazole 4 in 20 ml of 90% acetic acid is refluxed for 15 minutes. It is then poured into a mixture of ice and water and extracted with dichloromethane.

The resulting aqueous phase is rendered alkaline by means of an aqueous solution of 10N sodium hydroxide and extracted with chloroform. The combined organic phases are evaporated and the residue is dried by addition of toluene and azeotropic distillation. The resultant oil is dispersed in ether, which yields 4(5)-(2,2-diphenylethyl)-5(4)-methylimidazole in the form of a white solid which is filtered and dried under reduced pressure.

M.p. 217°–218° C.

| Elementary analysis: | C | H | N |
|---|---|---|---|
| $C_{18}H_{18}N_2$ % calculated | 80.7 | 7.0 | 10.5 |
| % found | 81.0 | 6.9 | 10.3 |

EXAMPLE 2

Synthesis of 4(5)-{[2-(2-fluorophenyl)-2-(4'-fluorophenyl)]ethyl}imidazole (hydrochloride) 4.

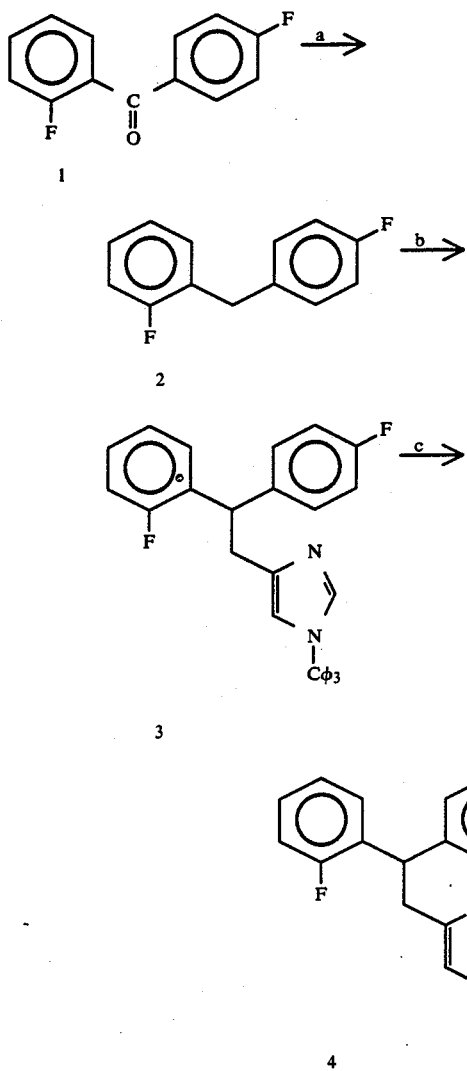

a. Synthesis of 2,4'-difluorophenyl methane 2.

100 ml of ethanol and 1.1 g of 10% palladium on carbon are introduced into a Parr apparatus of 1 l. Then a solution of 10.90 g (50 mmol) of 2,4'-difluorobenzophenone in 100 ml of the preceding solvent and 1 ml of a saturated solution of hydrochloric acid in methanol are added. The mixture is hydrogenated under a pressure of 2.75 bars for 2 hours at 0° C. The obtained medium is filtered then evaporated to dryness under reduced pressure.

The product thus obtained is purified by distillation under reduced pressure.

B.p. 66°-70° C./4.10⁻mbar.

b. Synthesis of 4-{[2-(2-fluorophenyl)-2-(4'-fluorophenyl)]-ethyl}-1-tritylimidazole 3.

Sodium is added in small portions into a reactor containing 50 ml of liquid ammonia and swept by a slight current of nitrogen, until a persistent blue coloration is obtained. A few crystals of iron-III nitrate are added to the solution, folowed by a supplementary quantity of 253 mg of metallic sodium. The medium is stirred at −75° C. for 30 minutes, before the slow addition of a solution of 2.04 g (10 mmols) of 2,4'-difluorophenylmethane in 5 ml of ether then, after a further half hour, a solution of 3.21 g (9 mmols) of 1-trityl-4-chloromethylimidazole in 20 ml of THF. Accordingly the ammonia is allowed to evaporate spontaneously, then 30 ml of water are added to the residue, which is then extracted three times with methylene chloride. The combined extracts are dried and evaporated to dryness under reduced pressure.

The product is introduced as such into the following step.

c. The preceding tritylated derivative is mixed with 20 ml of acetic acid at 90%, heated for 5 minutes to reflux temperature then evaporated to dryness under reduced pressure. The residue is shared between methylene chloride and 5% aqueous sodium hydrogen carbonate. The aqueous phase is again sodium hydrogen carbonate. The aqueous phase is again extracted twice and the combined organic extracts are dried and evaporated. The residue is taken up in ether and the solution is saturated with anhydrous gaseous hydrochloric acid. The precipitated hydrochloride is filtered and precipitated again in a mixture of acetonitrile and ether.

M.p. 141°-141.5° C.

| Elementary analysis: | | C | H | N |
|---|---|---|---|---|
| $C_{17}H_{14}F_2N_2 \cdot HCl$ | % calculated | 63.7 | 4.7 | 8.7 |
| | % found | 63.6 | 4.7 | 8.8 |

EXAMPLE 3

Synthesis of 4(5)-(2,2-diphenylethyl)-2-methylimidazole 3.

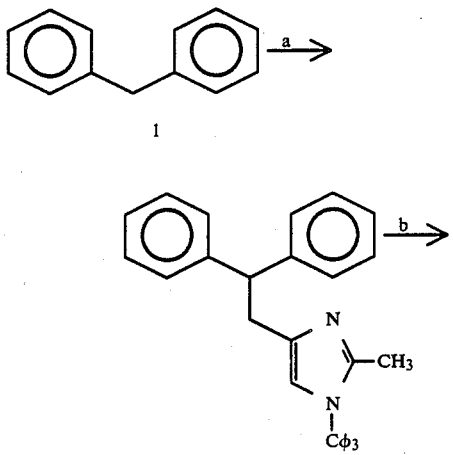

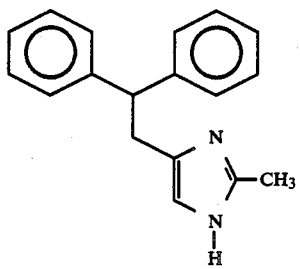

3 a. Synthesis of 4-(2,2-diphenylethyl)-2-methyl-1-tritylimidazole 2.

Under an inert atmosphere (nitrogen), 16.8 ml of t-butyllithium (1.7M solution in hexane) are added to 4.30 g (26 mmols) of diphenyl methane dissolved in 50 ml of THF. The mixture is cooled by means of an ice bath, then again a solution of 5.00 g (12.9 mmols) of 4-chloromethyl-2-methyl-1-tritylimidazole in 30 ml of THF is added. After one night of stirring at room temperature, 40 ml of a saturated aqueous solution of sodium chloride and then 100 ml of water are added to the medium. The aqueous phase is extracted three times with methylene chloride then the combined extracts are dried and evaporated to dryness under reduced pressure. The residue is used as such in the following step.

b. The above obtained tritylated derivative is refluxed for 5 minutes in 100 ml of 90% acetic acid.

The solution obtained is evaporated to dryness under reduced pressure. 200 ml of water are added to the residue and the resulting suspension is filtered. The filtrate is neutralised by means of 5% aqueous sodium carbonate then extracted three times with methylene chloride. The evaporation of the combined extracts furnishes a solid which is purified by crystallisation in acetonitrile.

M.p. 168°–170° C.

| Elementary analysis: | | C | H | N |
|---|---|---|---|---|
| $C_{18}H_{18}N_2$ | % calculated | 82.4 | 6.9 | 10.7 |
| | % found | 82.3 | 6.9 | 10.7 |

EXAMPLE 4

Synthesis of 4(5)-[2-(1,1-diphenyl-2-methoxy)-pentyl]imidazole 6.

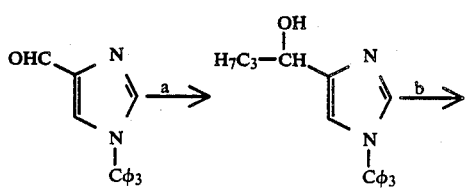

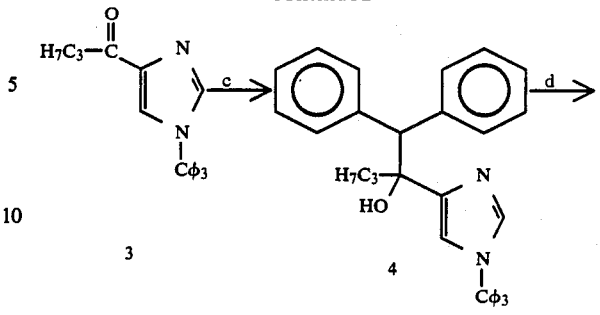

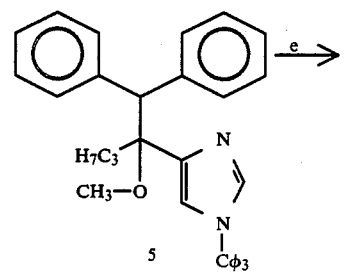

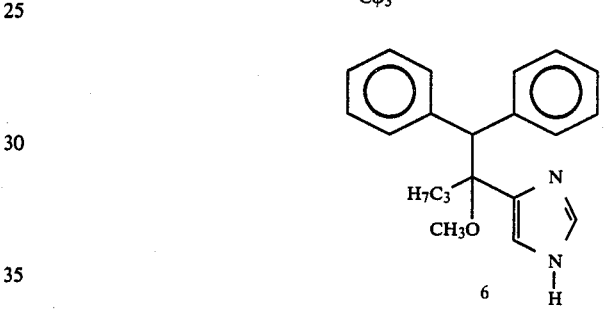

a. Synthesis of 4-[1-(1-hydroxy-butyl)]-1-tritylimidazole 2.

To 0.80 g (32.6 m moles) of magnesium turnings kept under an inert atmosphere (nitrogen) there are added an iodine crystal then a solution of 4.00 g (2.95 ml; 32.6 mmols) of 1-bromopropane in 25 ml of anhydrous diethyl ether, at such a speed that the mixture is kept at reflux temperature. At the end of the addition the medium having returned to room temperature is cooled by means of an ice bath. Then a solution of 5.50 g (16.3 mmols) of 1-trityl-4-imidazole carboxaldehyde in 50 ml of THF is added slowly. The mixture is stirred for 2 hours at room temperature, then 100 ml of a saturated aqueous solution of ammonium chloride are added. The aqueous phase is extracted with diethyl ether and, after drying, the extracts are evaporated to dryness under reduced pressure. The residue, which crystallises spontaneously, is recrystallised in ethyl acetate.

M.p. 154°–155° C.

b. Synthesis of 4-butanoyl-1-trityl-imidazole 3.

150 ml of dioxane and 11.00 g (10 eq.) of manganese dioxide are added to 4.75 g (12.4 mmols) of alcohol 2. The mixture is heated for 1 hour to reflux temperature then returned to room temperature before being filtered over a bed of celite. The filtrate is evaporated to dryness under reduced pressure and the residue is recrystallised in cyclohexane.

M.p. 134°–136° C.

c. Synthesis of 4-[2-(1,1-diphenyl-2-hydroxy)-pentyl]-1-tritylimidazole 4.

A solution of 4.30 g (25.8 mmols) of diphenylmethane in 50 ml of THF is prepared in inert atmosphere (nitrogen) then cooled in an ice bath. First 16.7 ml of butyllithium of a 1.7M solution in hexane and then, drop by drop, a solution of 4.90 g (12.9 mmols) of the previous ketone 3 in 50 ml of THF, are added slowly. The resultant mixture is stirred for 2 hours at room temperature and then 50 ml of a saturated aqueous solution of ammonium chloride and 100 ml of water are added. Extraction with ethyl acetate followed by evaporation of the previously dried extracts yields alcohol 4 which is recrystallised in cyclohexane.

M.p. 196°–198° C.

d. Synthesis of 4-[2-(1,1-diphenyl-2-methoxy)-pentyl]-1-tritylimidazole 5.

6.00 g (11 mmols) of 4 and 60 ml of THF are mixed under inert atmosphere (nitrogen). To this mixture, cooled in an ice bath, there are added 7 ml of butyllithium (1.7M in hexane), then 3.12 g (1.38 ml; 22 mmols) of methyl iodide. The mixture is stirred at room temperature for 0.5 hour before the addition of 50 ml of a saturated aqueous solution of ammonium chloride and 50 ml of water.

The aqueous phase is extracted with diethyl ether. The extracts are dried and evaporated to yield a residue which is used as such in the following step.

e. The previous tritylated derivative is treated with 30 ml of 66% aqueous acetic acid and the mixture is heated to reflux temperature until complete dissolution. The mixture is returned to room temperature, then cooled in a bath of ice water. The precipitate which is formed is filtered. The filtrate is neutralised by means of 5% aqueous sodium carbonate and extracted three times with ether.

The extracts are dried and evaporated to dryness under reduced pressure. The residue is finally recrystallised in acetonitrile to yield the desired product 6.

M.p. 161°–163° C.

| Elementary analysis: | | C | H | N |
|---|---|---|---|---|
| $C_{21}H_{24}N_2O$ | % calculated | 78.7 | 7.6 | 8.7 |
| | % found | 78.9 | 7.6 | 8.8 |

EXAMPLE 5

Synthesis of 4(5)-[(2,2-diphenyl-1-n.propyl)-ethenyl]-imidazole 3.

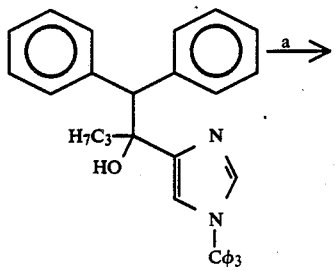

1

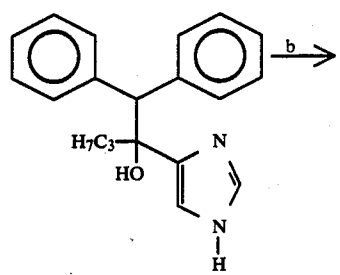

2

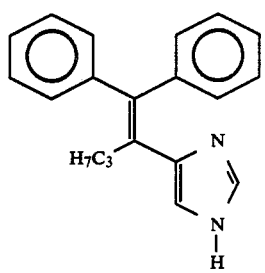

3 a. Synthesis of 4(5)-[2-(1,1-diphenyl-2-hydroxy)pentyl]imidazole 2.

A mixture of 5.00 g (9.1 mmols) of 4-[2-(1,1-diphenyl-2-hydroxy)-pentyl]-1-tritylimidazole 1 (see example 4) and 20 ml of 90% aqueous acetic acid is heated for 1 hour at reflux temperature. After return to room temperature the mixture is evaporated under reduced pressure. The residue is taken up in water and the aqueous phase is extracted with methylene chloride. The combined extracts are dried and evaporated to dryness under reduced pressure. The crude product (2) thus obtained is used as such in the following step.

b. 110 ml of hydrobromic acid (33% in acetic solution) are added to 3.00 g (8.8 mmols) of the alcohol 2. The mixture is stirred for 16 hours at room temperature, then it is diluted with 100 ml of water and neutralised with 1N aqueous NaOH. The aqueous phase is extracted with diethyl ether. The combined extracts are dried and evaporated to dryness under reduced pressure. The residue is purified by recrystallisation in ethyl acetate.

M.p. 187°–188° C.

| Elementary analysis: | | C | H | N |
|---|---|---|---|---|
| $C_{20}H_{20}N_2$ | % calculated | 83.3 | 7.0 | 9.7 |
| | % Found | 83.3 | 7.1 | 9.7 |

EXAMPLE 6

Synthesis of 4(5)-[2-(1,1-diphenyl)pentyl]imidazole 2.

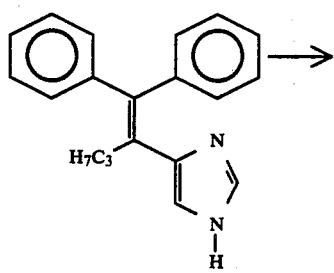

1

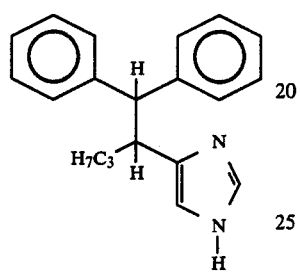

2

0.80 g (2.8 mmols) of 4(5)-[(2,2-diphenyl-1-n.propyl)-ethenyl]imidazole (see example 5) are hydrogenated in 200 ml of ethanol for 6 hours in the presence of 0.13 g of 10% palladium over carbon, at 2.72 bar and 70° C. The reaction medium is filtered and the filtrate is evaporated to dryness under reduced pressure. Diethylether is added to the residue and the insoluble part is filtered and eliminated. The filtrate is evaporated to dryness under reduced pressure and the residue is purified by crystallisation in heptane.

M.p. 116°–119° C.

| Elementary analysis: | | C | H | N | H$_2$O |
|---|---|---|---|---|---|
| C$_{20}$H$_{22}$N$_2$ | % calculated | 81.3 | 7.7 | 9.5 | — |
| (1.7% H$_2$O) | % found | 81.5 | 8.0 | 9.2 | 1.7 |

EXAMPLE 7

Synthesis of 4(5)-(2,2-diphenylethyl)-imidazole 3.

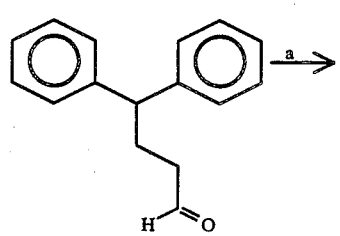

1

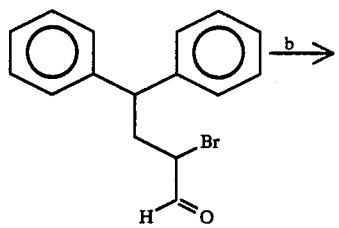

2

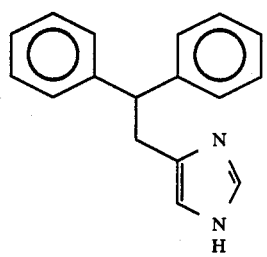

3 a. 45.6 g of 4,4-diphenylbutanal 1 (0.2 mol), 200 ml of anhydrous ether and 0.7 ml of dioxane are introduced under nitrogen atmosphere into a 500 ml flask. Several drops of bromine are added to this solution. When the solution has lost colour, 10.42 ml of bromine (0.2 mol) are added drop by drop in 90 minutes at such a rate that the solution remains colourless. At the end of the addition the reaction mixture is neutralised by a saturated solution of Na$_2$CO$_3$, the etheral phase is decanted, washed 3 times with water and dried over MgSO$_4$. This solution is evaporated under reduced pressure and protected from light. The colourless oil obtained is introduced into the following step.

b. 470 ml of formamide are heated to 160° C. in a 1 liter flask under nitrogen atmosphere, the brominated aldehyde 2 is then added drop by drop. The mixture is heated for 4 hours at this temperature, cooled and poured into 1 liter of iced water. The pH value is adjusted to 2 by addition of concentrated HCl, the insoluble yellow solid is filtered, the aqueous phase is extracted by CH$_2$Cl$_2$ and made alkaline (pH 10) by means of 4N NaOH. The white solid formed is filtered and recrystallised once in acetonitrile and once in toluene.

M.p. 158° C.

| Elementary analysis: | | C | H | N |
|---|---|---|---|---|
| C$_{17}$H$_{16}$N$_2$ | % calculated | 82.2 | 6.5 | 11.3 |
| | % found | 82.1 | 6.5 | 11.3 |

EXAMPLE 8

Synthesis of 4(5)-(2,2-diphenylethyl)-imidazole.

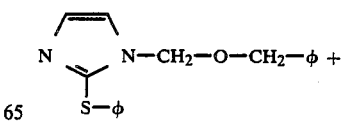

1

-continued

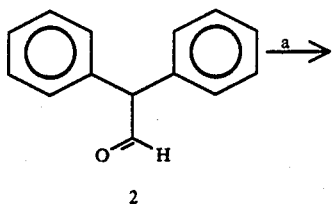
2

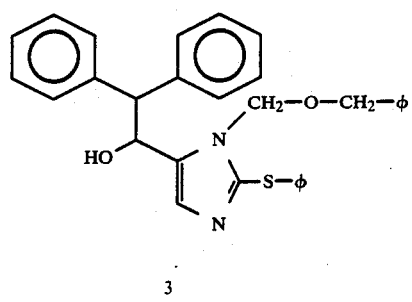
3

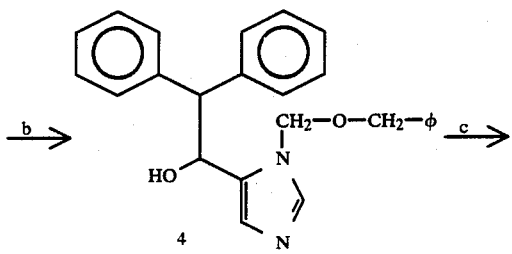
4

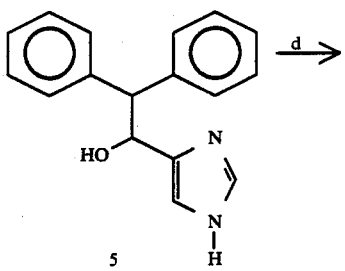
5

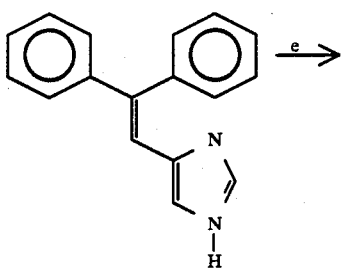
6

-continued

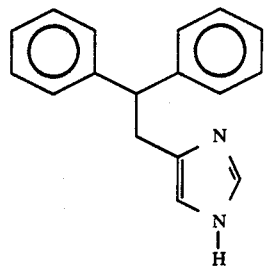
7 a. 9 g of 1-benzyloxymethyl-2-phenylthio-imidazole 1 (30 mM) and 150 ml of anhydrous THF are introduced into a 500 ml flask under nitrogen atmosphere. Then 25.6 ml of a 1.6 molar solution of butyllithium (41 mM) are added to the solution cooled to −78° C. After two hours at −65° C., 7.1 ml of diphenylacetaldehyde (40 mM) are added and the mixture is left overnight to return to room temperature. Then a saturated aqueous solution of ammonium chloride is added. The organic phase is decanted, dried over MgSO$_4$ and evaporated. The residual oil is purified by preparative HPLC (SiO$_2$/CH$_2$Cl$_2$/CH$_3$OH/100/1).

A white powder is obtained which melts at 60°–61° C.

b. 5 g of 3 are brought to reflux in ethanol in the presence of 5 g of Raney nickel during 5 hours. Then the Raney nickel is filtered, the ethanol is evaporated and the residue is shared between water and dichloromethane. The organic phase washed with water is dried over MgSO$_4$ and evaporated, the obtained solid is washed with toluene.

M.p. 183°–184° C.

c. 2 g of 4 are dissolved in a mixture of 125 ml of ethanol and 125 ml of 11N HCl, this solution is hydrogenated at 80° C. in the presence of 200 mg of Pd/C at 10%.

After absorption of one equivalent of hydrogen, the catalyst is filtered and the solvents are evaporated to dryness.

d. 700 mg of 5 are brought to reflux in 10 ml of trifluoroacetic acid. After 24 hours the trifluoroacetic acid is evaporated and the residue is introduced as such into the following step.

e. 700 mg of 6 are hydrogenated in ethanol at 60° C. under 3.1 bars for 5 hours in the presence of 100 mg of 10% Pd/C. After absorption of one equivalent of hydrogen, the catalyst is filtered, the solvent is evaporated and the residual oil is shared between 1N NaOH and ethyl acetate. The organic phase, washed with water, is dried over MgSO$_4$ and evaporated to dryness. The solid obtained is recrystallised in toluene.

M.p. 157° C.

Table I below lists the derivatives of the above examples and other derivatives according to the invention prepared according to the processes given above. All the compounds listed in Table I give a correct C, H, N elementary analysis and their structures have been verified by N.M.R. spectroscopy and mass spectrometry.

TABLE I

| Compound No. | X¹ | X² | Y¹ | Y² | R¹ | R² | R³ | R⁴ | R⁵ | Melting point (°C.) | Recrystallisation solvent |
|---|---|---|---|---|---|---|---|---|---|---|---|
| 1 | H | H | H | H | H | H | H | H | H | 158–159 | toluene |
| 2 | H | H | H | H | —$^{(1)}$ | | CH$_3$ | H | H | 166 | toluene |
| 3 | H | H | H | H | H | OH | CH$_3$ | H | H | 183–184 | toluene |
| 4 | H | H | H | H | H | H | CH$_3$ | H | H | 190 | toluene |
| 5 | H | H | H | H | H | OH | H | H | H | 177–178 | CH$_3$CN |
| 6 | H | H | H | H | H | CH$_3$O | H | H | H | 170 | CH$_3$CN |
| 7 | H | H | H | H | H | H | H | CH$_3$ | H | 217–218 | ether |
| 8 | H | H | H | H | C$_6$H$_5$ | | H | H | H | 290–300$^{(2)(3)}$ | EtOH |
| 9 | 3-CH$_3$ | H | H | H | H | H | H | H | H | 140$^{(3)}$ | i.C$_3$H$_7$—OH/ether |
| 10 | H | H | H | H | CH$_3$ | H | H | H | H | 153 | CH$_3$CN |
| 11 | H | H | H | H | —$^{(1)}$ | | H | H | H | 170–171 | MeOH—H$_2$O |
| 12 | 2-CH$_3$ | H | H | H | H | H | H | H | H | 182$^{(3)}$ | CH$_3$CN/ether |
| 13 | 2-Cl | H | H | H | H | H | H | H | H | 159$^{(3)}$ | CH$_3$CN/ether |
| 14 | 4-F | H | H | H | H | H | H | H | H | 157 | CH$_3$CN |
| 15 | 2-F | H | 4'-F | H | H | H | H | H | H | 141–141.5$^{(3)}$ | CH$_3$CN/ether |
| 16 | 2-CH$_3$ | 5-CH$_3$ | H | H | H | H | H | H | H | 171$^{(3)}$ | CH$_3$CN |
| 17 | 4-OCH$_3$ | H | H | H | H | H | H | H | H | 142 | CH$_3$CN |
| 18 | H | H | H | H | —$^{(1)}$ | | n.C$_3$H$_7$ | H | H | 187–188 | ethyl acetate |
| 19 | H | H | H | H | H | H | n.C$_3$H$_7$ | H | H | 116–119 | heptane |
| 20 | H | H | H | H | H | CH$_3$O | n.C$_3$H$_7$ | H | H | 161–163 | CH$_3$CN |
| 21 | 4-CH$_3$ | H | H | H | H | H | H | H | H | 219$^{(3)}$ | CH$_3$CN/ether |
| 22 | 3-CH$_3$ | 4-CH$_3$ | H | H | H | H | H | H | H | 187$^{(3)}$ | CH$_3$CN |
| 23 | 4-OCH$_3$ | H | 4'-OCH$_3$ | H | H | H | H | H | H | 178–179$^{(3)}$ | CH$_3$CN |
| 24 | 2-CH$_3$ | 4-CH$_3$ | H | H | H | H | H | H | H | 245–246$^{(3)}$ | isopropanol |
| 25 | H | H | H | H | H | H | H | H | CH$_3$ | 168–170 | CH$_3$CN |
| 26 | H | H | H | H | H | CH$_3$O | H | H | CH$_3$ | 177–179 | CH$_3$CN |
| 27 | 2-F | 6-F | H | H | H | H | H | H | H | 193$^{(3)}$ | CH$_3$CN |
| 28 | 2-F | H | H | H | H | H | H | H | H | 161$^{(3)}$ | CH$_3$CN |
| 29 | 4-C$_6$H$_5$ | H | H | H | H | H | H | H | H | 192 | CH$_3$CN |
| 30 | 2-COOH | H | H | H | H | H | H | H | H | 258 (dec) | DMF |
| 31 | 2-COOCH$_3$ | H | H | H | H | H | H | H | H | 161$^{(3)}$ | CH$_3$CN/ether |

TABLE I-continued

| Compound No. | X¹ | X² | Y¹ | Y² | R¹ | R² | R³ | R⁴ | R⁵ | Melting point (°C.) | Recrystallisation solvent |
|---|---|---|---|---|---|---|---|---|---|---|---|
| 32 | 4-COOH | H | H | H | H | H | H | H | H | 212 (dec) | isopropanol |

Remarks.
[1] The substituents $R_1$ and $R_2$ together represent a carbon-carbon bond in such manner that these compounds of formula I correspond to the following formula I':

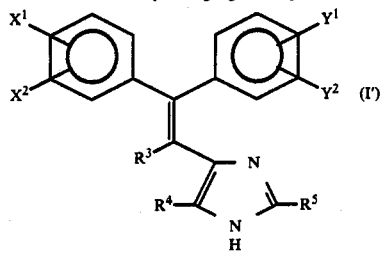

[2] decomposition.
[3] hydrochloride.

The acute toxicity of the compounds of the present invention was studied after oral administration to mice. The products to be tested, suspended in a 1% tragacanth gum mucilage, were administered by means of an intragastric probe to groups of three male mice which had fasted since the preceding day. The doses tested are a function of the effect observed and can vary from 3,000 to 3 mg/kg or less. The mortality was recorded for 15 days. The lethal dose for 50% of the animals (LD$_{50}$) was calculated according to the method of J. Litchfield and F. Wilcoxon, J. Pharmacol. Exp. Ther., 96, 99 (1949) and expressed in mg/kg. The results are indicated in Table IV, pp. 59-60. The effect of the products on the behaviour of the animals is observed until 5 to 6 hours after the treatment indicated above and after 24 hours, using a method derived from that of S. Irwin, described by R. A. Turner, Screening Methods in Pharmacology, Chapter 3, pages 22-34, Academic Press, 1965. If anomalies are noted, the observation is prolonged and smaller doses are tested.

No important side effect upon the behaviour was observed for the majority of the compounds.

The compounds of the present invention have been subjected to a series of in vitro and in vivo tests to determine their biological activity and therapeutic utility. The essential activity of importance resides in the $\alpha_2$ receptor antagonist activity. Such activity indicates therapeutic utility for indications of disorders of the central nervous system, e.g., depression, mental disorders and epilepsy. In addition, a number of the present compounds show low or insignificant affinity for $\alpha_1$ receptor sites as indicated by in vitro receptor binding assays. This property indicates additional benefit, particularly with respect to diminished cardiovascular side effects. The results of these biological tests are summarized in Table II. The tests were carried out as described below.

Column 3 summarizes the binding activities of the compounds tested, for $\alpha_1$ and $\alpha_2$ adrenergic receptors. Column 4 summarizes the in vitro activities of the compounds evaluated in a guinea pig ileum model. Column 5 summarizes the $\alpha_2$ antagonist effects of the compounds in an in vivo animal model. Column 6 summarizes an anticonvulsant activity tested in an in vivo model.

The activity of the compounds according to the invention with respect to binding of the $\alpha$-adrenergic receptors was determined in vitro according to a method deriving from the works of B. R. Rouot et al., Life Sci., 25, 769 (1979) and of D. U'Prichard et al., Mol. Pharmacol., 13, 454 (1977). This method consists in measuring the binding to the receptor on rat brain homogenates, by marking by means of a specific tritriated ligand placed in competition with the product to be tested.

In the presenct case the binding to the $\alpha_1$-adrenergic receptors was measured by means of 1.6 nM of $^3$H-WB 4101 and the binding to the $\alpha_2$-adrenergic receptors by means of 0.7 nM of $^3$H-p. aminoclonidine, the non-specific binding being determined by 1,000 nM of phentolamine. The results are given in Table II, column 3, and are expressed in terms of percentage of inhibition of the specific binding of $10^{-7}$ molar compound concentration. The results indicate that the compounds according to the invention have low affinity for the $\alpha_1$ receptors since the percentage of inhibition of the specific binding on the $\alpha_1$ receptors is generally low.

The high percentage of inhibition of the specific binding of the $\alpha_2$-adrenergic receptors presented by a large number of the compounds tested indicates that the compounds according to the invention exhibit a considerable affinity for the $\alpha_2$ receptors.

As shown in column 3, the compound Nos. 1, 9, 13, 27 and 28 exhibit a high affinity for $\alpha_2$ receptors in the in vitro binding assay.

The $\alpha_2$ antagonist and $\alpha_2$ agonist activity of the compounds according to the invention was determined upon isolated organs according to a model described by G. M. Drews, Br. J. Pharmaco., 64, 293-300 (1978).

This model is based upon the principle that the stimulation of the cholinergic nervous transmissions of the guinea pig ileum causes the liberation of acetyl choline, which in turn causes contractions of the ileum.

The stimulation of the $\alpha_2$-adrenergic receptors inhibits the activity of the cholinergic nerve and consequently reduces all response resulting from a timulation of the latter. Thus the contractions of the ileum induced by electric stimulation of the tissue are inhibited by clonidine, an $\alpha_2$ agonist, in proportion to the dose. This inhibition is specifically displaced by the $\alpha_2$ antagonists and not by the $\alpha_1$ antagonists.

The method utilized can be summarized as follows: three dose-response curves to clonidine are established at an interval of 60 minutes. Two concentrations of the product to be tested are added successively 10 minutes before the realization of the second and third clonidine curves. Next, after washing, a dose-response curve is established with the product to be tested.

The dose-response curves are calculated as a percentage of the maximum inhibition obtained for the first curve. In this system the products having an $\alpha_2$ antagonist activity displace the dose-response curve to clonidine. The $\alpha_2$ antagonist activity, expressed in $pA_2$ value, shown in column 4, is calculated according to J. M. Van Rossum, Arch. Int. Pharmacodyn., 143, 299–300 (1963).

A reduction of the contractions induced by the tested product alone indicates an $\alpha_2$ agonist effect. This activity is expressed in—log $ED_{50}$ (the—logarithm of the concentration of the product giving 50% of the maximum inhibition obtained with clonidine).

The results of these tests, expressed as $pA_2$ and—log $ED_{50}$ values are summarized in Table II, column 4, below. The higher the $pA_2$ value, the higher the $\alpha_2$ antagonist activity; the higher the—log $ED_{50}$ value (i.e., the $pA_2$ agonist activity), the higher the $\alpha_2$ agonist activity. Calculated on a log scale as summarized in Table II, these results indicate that the compounds of the present invention have high $\alpha_2$ antagonist activity and significant $\alpha_2$ agonist activity.

The antogonist effect on peripheral vascular $\alpha_2$ receptors was demonstrated in biological experiments carried out on pithed rats.

The $\alpha_2$ antagonist activity of the compounds is evaluated by the inhibition of the pressor effect (blood pressure elevation), of a specific $\alpha_2$ agonist agent, 4H-Thiazolo[4,5-b]azetin-2-amine, 5,6,7,8-tetrahydro-6-(2-propenyl)-, dihydrochloride, designated as BHT 920 at a concentration of 30 $\mu$g/kg i.v.) according to a method described by J. C. Van Meel et al., J. Pharmacol. Exp. Ther., 219, 760–767 (1981).

The compound to be tested is administered at 1 mg/kg i.v. The ability of the compounds tested to antagonize the pressor effects of BHT 920 is determined and expressed as percentage of inhibition. Any direct hypertensive ($=\alpha_2$ agonist) activity of the compounds under test can likewise be detected. In this test, several compounds according to the invention have shown themselves very active as $\alpha_2$ antagonist agents, in particular compounds Nos. 1, 4, 7, 9, 12, 13, 14, 15, 17, 21, 22 and 23.

The activity of the compounds according to the invention on the central nervous system was evaluated under four experimental conditions by examining the effect upon:
the antihypertensive action of clonidine (Table II, column 5)
convulsions caused by bicuculline (Table II, column 6)
the locomotive depression induced by clonidine,
the serotoninergic system.

In the first study, carried out upon unanaesthetized spontaneously hypertensive rats (SHR rats), the ability of the compounds of the present invention to inhibit the antihypertensive action of clonidine was determined.

The antihypertensive activity of clonidine results from an interaction with $\alpha_2$ adrenergic receptors of the central nervous system, i.e., central antihypertensive actions.

In this test, two groups of SHR rats are utilized as follows. In the first group, prior to subcutaneous administration of clonidine (50 $\mu$g/kg), the SHR rats are treated with the compound to be tested (1 mg/kg p.o.) dissolved in a saline vehicle. The second group (control group) of SHR rats are treated with the saline vehicle only, prior to subcutaneous administration of clonidine.

The arterial pressure is measured in the region of the median coccygeal artery according to the method of J. Roba, A. F. DeSchaepdrijver, Exp. Anim., 4, 147–162 (1971).

The results of this assay summarized in Table II, column 5, are expressed as a percentage of inhibition of the effect of clonidine. The results show that the majority of the derivatives of the invention display a significant $\alpha_2$ antagonist effect as assessed in this in vivo model.

These results indicate that the compounds of the present invention are: (1) bioavailable to the central nervous system when administered by oral route; (2) able to influence central $\alpha_2$ receptor activity—as expressed by their ability to antagonize clonidine effects upon central $\alpha_2$ receptors; and (3) useful in the treatment of mental disorders in which $\alpha_2$ antagonist activity is a desirable pharmacological effect.

In the second study the anti-convulsant effect of the compounds of the present invention was examined in two seizure models; bicuculline-induced tonic extension in mice and 3-mercaptopropionic acid (3-MPA)-induced tonic extension in mice.

In the bicuculline study, the ability of the compounds of the present invention to protect against tonic extension (involving rigidity) was evaluated as follows. Each test compound was administered to a group of ten mice at a dose of 10 mg/kg, 3 hours prior to the i.v. administration of bicuculline (0.7 mg/kg). Anticonvulsant activity in this test is expressed as percentage of animals tested. The results are given in Table II, column 6, and indicate that several compounds display significant anticonvulsive activity in this test. The anticonvulsant effect of the compounds has also been tested with respect to the tonic extension induced by 3-mercaptopropionic acid (120 mg/kg subcutaneously) in mice.

In the 3-MPA assay, the compounds of the present invention are administered orally at a dose of 100 mg/kg 30 minutes prior to administration of 3-MPA. Each compound was tested on a group of 5 mice; if more than 1 mouse was protected, a second group of 5 mice was tested. In this test, several compounds of the invention exhibited a potent anticonvulsant effect (compounds Nos. 1, 3, 10, 13, 16, 24, 27, 28 and 29).

TABLE II

| | | Biological Data | | | | | |
| | | | | Column 4 | | | |
| Column 1 Compound No (1) | Column 2 LD$_{50}$ | Column 3 % Inhibition of the Specific Binding (2) at $10^{-7}$ M for | | $\alpha_2$ Antagonist Activity (pA$_2$) | $\alpha_2$ Agonist Activity (- log ED$_5$O) | Column 5 $\alpha_2$ Antagonist Effect (% Inhibition of the Antihypertension of Clonidine) | Column 6 Anticonvulsive effect (versus) Bicuculline) (% Protection) |
| | | $\alpha_1$ Recep. | $\alpha_2$ Recep. | | | | |
|---|---|---|---|---|---|---|---|
| 1 | 155 | 17 | 89 | 8.3 | 5.5 | 50 | 0 |
| 2 | | 3 | 43 | 7.3 | 5.6 | 71 | 20 |
| 3 | | 0 | 10 | | | 67 | 10 |

TABLE II-continued

Biological Data

| Column 1 Compound No (1) | Column 2 LD$_{50}$ | Column 3 % Inhibition of the Specific Binding (2) at $10^{-7}$ M for | | Column 4 | | Column 5 $\alpha_2$ Antagonist Effect (% Inhibition of the Antihypertension of Clonidine) | Column 6 Anticonvulsive effect (versus) Bicuculline) (% Protection) |
|---|---|---|---|---|---|---|---|
| | | $\alpha_1$ Recep. | $\alpha_2$ Recep. | $\alpha_2$ Antagonist Activity (pA$_2$) | $\alpha_2$ Agonist Activity (- log ED$_5$O) | | |
| 4 | >300 | 4 | 5 | 6.5 | <5.5 | 68 | 40 |
| 5 | >300 | 3 | 2 | | | 24 | 30 |
| 6 | | 0 | 0 | | | 62 | 30 |
| 7 | | 12 | 23 | 7.3 | 5.7 | 82 | 20 |
| 8 | 1.750 | 0 | 0 | | | 28 | 20 |
| 9 | 155 | 4 | 85 | 7.8 | 5.6 | 92 | 20 |
| 10 | | 0 | 6 | | | 46 | 27 |
| 11 | | 6 | 9 | | | 48 | 40 |
| 12 | 155 | 0 | 71 | 7.9 | 5.4 | 78 | 50 |
| 13 | 172 | 7 | 81 | 8.0 | 5.5 | 46 | 20 |
| 14 | 155 | 0 | 69 | 7.8 | 5.2 | 82 | 0 |
| 15 | 155 | 7 | 77 | 7.8 | 5.3 | 75 | 0 |
| 16 | >300 | 0 | 31 | 7.0 | 5.7 | 69 | 20 |
| 17 | 350 | 6 | 78 | 7.9 | 5.0 | 26 | 10 |
| 18 | 270 | 0 | 0 | | | 47 | 50 |
| 19 | 350 | 4 | 15 | | | 75 | 40 |
| 20 | >300 | 0 | 6 | | | 62 | 60 |
| 21 | 350 | 4 | 74 | 7.6 | 5.3 | 48 | 50 |
| 22 | 155 | 4 | 22 | | | 57 | 20 |
| 23 | | 0 | 20 | | | 40 | 10 |
| 24 | | 0 | 34 | | | 93 | 0 |
| 25 | | 0 | 3 | | | 87 | 10 |
| 26 | 350 | 1 | 2 | | | | 10 |
| 27 | 173 | 14 | 86 | | | | |
| 28 | 94 | 8 | 95 | | | | |
| 29 | >300 | 15 | 23 | | | | |
| 30 | >300 | 12 | 1 | | | | |
| 31 | | 13 | 20 | | | | |

(1) The numbers of the compounds correspond to the numbers of the compounds in Table I, indicated previously.
(2) The specific binding is the total binding less the non-specific binding. The total binding is the binding in the absence of non-radioactive drug. The non-specific binding is the binding in the presence of 1,000 nM of phentolamine. The products of the invention are tested at a concentration of $10^{-7}$ molar.

The third in vivo study evaluation activity of the compounds of the invention on clonidine induced depression of locomotor activity. The previously-discussed study involving clonidine related to its $\alpha_2$ agonist effects on the brain's regulation of the cardiovascular system.

The present study involved clonidine $\alpha_2$ agonist effects on central control of locomotor activity. Clonidine inhibits locomotor activity and rearing activity in the mouse. In this "open field" test, mice are pretreated with the compounds of the present invention at doses of 1 to 10 mg/kg p.o. (n=4), two hours prior to clonidine administration (0.3 mg/kg p.o.) Thirty minutes after the clonidine administration the animals are placed in a rectangular "open field" of 47×53 cm, the floor of which is divided into 36 boxes of about 8×9 cm. The number of boxes through which the animal goes in 3 minutes and the number of rearing episodes are noted. Each compound was evaluated for its ability to antagonize the effect of clonidine. Among the compounds according to the invention, compound No. 1 was particularly active in this test. Compound No. 1 antagonizes clonidine-induced depression of locomotor activity and rearing activity from 1 mg/kg p.o. and from 3 mg/kg p.o., respectively.

The effects of chronic administration of compound No. 1 were also evaluated in this test. In this study, groups of 5-6 mice were treated with compound No. 1 (3 mg/kg p.o.) either twice daily for 14 days (chronic) or with one single dose (acute). Clonidine-induced (0.15 mg/kg i.p.) locomotor depression was determined 1 h, 24 h and 72 h after the last treatment with compound No. 1, and the result expressed as % inhibition of clonidine actions.

The experimental results summarized in Table III show that after 14 days of repeated administration, compound No. 1 maintained activity in the "open field" test at the same level as after acute administration. This result indicates that $\alpha_2$ antagonist activity is maintained after chronic administration. Accumulation of the compound does not appear to occur because the activity in the "open field" test disappeared 24 hours after withdrawal of the drug.

TABLE III

Effect of Compound No. 1 on Locomotor Activity in the Open-field Test

| Treatment by Compound No. 1 | Time since Last Administration of the Drug | % Inhibition of the Effect of Clonidine on Locomotor Activity in Mice |
|---|---|---|
| acute admin. | 1 h. | 52 |
| chronic admin. | 1 h. | 59 |
| | 24 h. | 3 |
| | 72 h. | 5 |

The fourth in vivo study evaluated activity of the compounds of the invention on serotonin agonist-induced head twitching (serotoninergic syndrome). The compound 5-methoxy-N,N-dimethyl tryptamine is a serotonin agonist which induces head twitching in mice. The activity of this tryptamine compound is increased by antidepressant drugs. This study evaluated the ability of the compounds of the present invention to influence the effect of the tryptamine-induced head twitching (E. Friedman, et al., Eur. J. Pharmacol., 89, 69–76, 1983).

The compounds to be tested were administered to mice at the dose of 3 mg/kg p.o. either acutely or chronically twice a day continually for 2 weeks. The increased head twitching caused by the tryptamine compound (2 mg/kg i.p.) was observed 1, 24 and 72 hours after the last administration of the test compound.

The results obtained for compound No. 1 are summarized in Table IV hereafter.

TABLE IV

Effect of Compound No. 1 on Head Twitches Induced by 5-methoxy-N,N—dimethyltryptamine in Mice

| Treatment | Time Since the Last Treatment | Head Twitches/ 5 Minutes % (1) |
|---|---|---|
| Vehicle only | | 100 |
| Compound No. 1 (at 3 mg/kg p.o.) | | |
| acute | 1 h. | 171 |
| chronic | 1 h. | 278 |
| | 24 h. | 210 |
| | 72 h. | 211 |

(1) % = percent head twitches compared to the vehicle treated group.

What is claimed is:

1. A compound of the formula

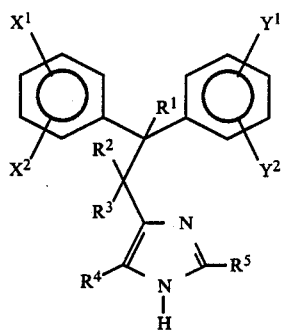

wherein:
$X^1$, $X^2$, $Y^1$, and $Y^2$, which may or may not be identical, are selected from the group consisting of hydrogen, fluoro, chloro, bromo, a linear or branched alkyl radical having from 1 to 3 carbon atoms, a linear or branched alkoxy radical having from 1 to 3 carbon atoms, carboxy, an alkoxy-carbonyl having from 1 to 3 carbon atoms, and phenyl;
$R^1$ and $R^2$ together form a carbon-carbon double bond;
$R^3$ is selected from the group consisting of hydrogen, hydroxyl, a linear or branched alkyl having from 1 to 6 carbon atoms, and a linear or branched alkoxy having from 1 to 4 carbon atoms;
$R^4$ and $R^5$, which may or may not be identical, are hydrogen or a linear or branched alkyl radical having from 1 to 3 carbon atoms; or a pharmaceutically-acceptable non-toxic salt of addition formed with a pharmaceutically usable acid.

2. The compound of claim 1, wherein $X^1$, $X^2$, $Y^1$ and $Y^2$, which may or may not be identical, are selected from the group consisting of hydrogen, fluoro, chloro, methyl, methoxy and phenyl.

3. The compound of claim 2, wherein at least two of the groups $X^1$, $X^2$, $Y^1$ and $Y^2$ are different from hydrogen.

4. The compound of claim 2, wherein at least $X^2$ and $Y^1$ are hydrogen.

5. The compound of claim 2, wherein $X^1$, $X^2$, $Y^1$ and $Y^2$ are hydrogen.

6. The compound of claim 2, wherein one or both of $X^1$ and $Y^1$ are fluoro.

7. The compound of claim 1, wherein $R^3$ is hydrogen or a linear or branched alkyl group having from 1 to 4 carbon atoms.

8. The compound of claim 1, wherein $R^4$ and $R^5$, which may or may not be identical, are hydrogen or methyl.

9. The compound of claim 1, wherein $R^4$ and $R^5$ are hydrogen.

10. The compound of claim 1, wherein $X^1$, $X^2$, $Y^1$, $Y^2$, $R^4$ and $R^5$ are hydrogen.

11. The compound of the claim 1, which is 4(5)-[2,2-diphenyl-1-methyl)ethenyl]imidazole.

12. The compound of the claim 1, which is 4(5)-[2,2-diphenyl)ethenyl]imidazole.

13. The compound of the claim 1, which is 4(5)-[2,2-diphenyl-1-n.propyl)ethenyl]imidazole.

14. A therapeutic method for blocking $\alpha_2$-adrenergic receptors in an individual when such therapy is indicated, comprising administering to the individual an $\alpha_2$-adrenergic receptor blocking amount of a compound of the formula:

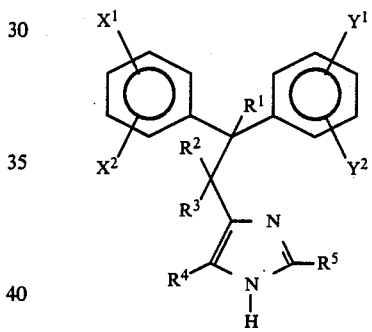

wherein:
$X^1$, $X^2$, $Y^1$, and $Y^2$, which may or may not be identical, are selected from the group consisting of hydrogen, fluoro, chloro, bromo, a linear or branched alkyl radical having from 1 to 3 carbon atoms, a linear or branched alkoxy radical having from 1 to 3 carbon atoms, carboxy, an alkoxy-carbonyl having from 1 to 3 carbon atoms, and phenyl;
$R^1$ is selected from the group consisting of hydrogen, methyl and phenyl;
$R^2$ and $R^3$, which may or may not be identical, are selected from the group consisting of hydrogen, hydroxyl, a linear or branched alkyl having from 1 to 6 carbon atoms, and a linear or branched alkoxy having from 1 to 4 carbon atoms;
$R^1$ and $R^2$ can together form a carbon-carbon double bond;
$R^4$ and $R^5$, which may or may not be identical, are hydrogen or a linear or branched alkyl radical having from 1 to 3 carbon atoms; or a pharmaceutically-acceptable non-toxic salt of addition formed with a pharmaceutically usable acid.

15. The method of claim 14, wherein $X^1$, $X^2$, and $Y^1$ and $Y^2$, which may or may not be identical, are selected from the group consisting of hydrogen, fluoro, chloro, methyl, methoxy and phenyl.

16. The method of claim 15, wherein at least two of the groups $X^1$, $X^2$, $Y^1$ and $Y^2$ are different from hydrogen.

17. The method of claim 15, wherein at least $X^2$ and $Y^1$ are hydrogen.

18. The method of claim 15, wherein $X^1$, $X^2$, $Y^1$ and $Y^2$ are hydrogen.

19. The method of claim 15, wherein one or both of $X^1$ and $Y^1$ are fluoro.

20. The method of claim 15, wherein $R^1$ is hydrogen or a methyl group and $R^2$ is selected from the group consisting of hydrogen, hydroxyl, methyl and methoxy.

21. The method of claim 14, wherein $R^1$ and $R^2$ together form a carbon-carbon double bond.

22. The method of claim 14, wherein $R^3$ is hydrogen or a linear or branched alkyl group having from 1 to 4 carbon atoms.

23. The method of claim 14, wherein $R^4$ and $R^5$, which may or may not be identical, are hydrogen or methyl.

24. The method of claim 14, wherein $R^1$, $R^2$, $R^4$ and $R^5$ are hydrogen.

25. The method of claim 14, wherein $X^1$, $X^2$, $Y^1$, $Y^2$, $R^1$, $R^4$ and $R^5$ are hydrogen.

26. The method of claim 14, wherein said compound is selected from the group consisting of:
4(5)-(2,2-diphenylethyl)imidazole;
4(5)-[(2,2-diphenyl-1-methyl)ethenyl]imidazole;
4(5)-[2-(3-methylphenyl)-2-phenyl]ethylimidazole;
4(5)-[2-(2-chlorophenyl)-2-phenyl]ethylimidazole;
4(5)-[2-(4-fluorophenyl)-2-phenyl]ethylimidazole;
4(5)-[2-(2-fluorophenyl)-2-(4'-fluorophenyl)]ethylimidazole;
4(5)-[2-(4-methoxyphenyl)-2-phenyl]ethylimidazole;
4(5)-[(2,2-diphenyl-1-n.propyl)ethenyl]imidazole;
4(5)-[2-(1,1-diphenyl-pentyl]imidazole;
4(5)-[2-(1,1-diphenyl-2-methoxy)pentyl]imidazole;
4(5)-[(2,2-diphenylethyl)-2-methyl]imidazole;
4(5)-[(2,2-diphenylethyl)-5(4)-methyl]imidazole;
4(5)-[2-(2-fluorophenyl)-2-(6'-fluorophenyl)]ethylimidazole;
4(5)-[2-(2-fluorophenyl)-2-phenyl]ethylimidazole;
4(5)-[2-(4-biphenyl)-2-phenyl]ethylimidazole;
4(5)-[1-(2,2-diphenyl)-propyl]imidazole;
4(5)-[2-(2-methylphenyl)-2-(5'-methylphenyl)]ethylimidazole;
4(5)-[2-(2-methylphenyl)-2-(4'-methylphenyl)]ethylimidazole.

27. A therapeutic method for treating convulsions in an individual when such therapy is indicated, comprising administering to the individual a therapeutically effective amount of a compound of the formula:

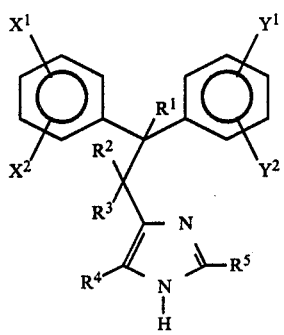

wherein:

$X^1$, $X^2$, $Y^1$, and $Y^2$, which may or may not be identical, are selected from the group consisting of hydrogen, fluoro, chloro, bromo, a linear or branched alkyl radical having from 1 to 3 carbon atoms, a linear or branched alkoxy radical having from 1 to 3 carbon atoms, carboxy, an alkoxy-carbonyl having from 1 to 3 carbon atoms, and phenyl;

$R^1$ is selected from the group consisting of hydrogen, methyl and phenyl;

$R^2$ and $R^3$, which may or may not be identical, are selected from the group consisting of hydrogen, hydroxyl, a linear or branched alkyl having from 1 to 6 carbon atoms, and a linear or branched alkoxy having from 1 to 4 carbon atoms;

$R^1$ and $R^2$ can together form a carbon-carbon double bond;

$R^4$ and $R^5$, which may or may not be identical, are hydrogen or a linear or branched alkyl radical having from 1 to 3 carbon atoms; or a pharmaceutically-acceptable non-toxic salt of addition formed with a pharmaceutically usable acid.

28. The method of claim 27, wherein $X^1$, $X^2$, and $Y^1$ and $Y^2$, which may or may not be identical, are selected from the group consisting of hydrogen, fluoro, chloro, methyl, methoxy and phenyl.

29. The method of claim 28, wherein at least two of the groups $X^1$, $X^2$, $Y^1$ and $Y^2$ are different from hydrogen.

30. The method of claim 28, wherein at least $X^2$ and $Y^1$ are hydrogen.

31. The method of claim 28, wherein $X^1$, $X^2$, $Y^1$ and $Y^2$ are hydrogen.

32. The method of claim 28, wherein one or both of $X^1$ and $Y^1$ are fluoro.

33. The method of claim 28, wherein $R^1$ is hydrogen or a methyl group and $R^2$ is selected from the group consisting of hydrogen, hydroxyl, methyl and methoxy.

34. The method of claim 27, wherein $R^1$ and $R^2$ together form a carbon-carbon double bond.

35. The method of claim 27, wherein $R^3$ is hydrogen or a linear or branched alkyl group having from 1 to 4 carbon atoms.

36. The method of claim 27, wherein $R^4$ and $R^5$, which may or may not be identical, are hydrogen or methyl.

37. The method of claim 27, wherein $R^1$, $R^2$, $R^4$ and $R^5$ are hydrogen.

38. The method of claim 27, wherein $X^1$, $X^2$, $Y^1$, $Y^2$, $R^1$, $R^4$ and $R^5$ are hydrogen.

39. The method of claim 27, wherein said compound is selected from the group consisting of:
4(5)-(2,2-diphenylethyl)imidazole;
4(5)-[(2,2-diphenyl-1-methyl)ethenyl]imidazole;
4(5)-[2-(3-methylphenyl)-2-phenyl]ethylimidazole;
4(5)-[2-(2-chlorophenyl)-2-phenyl]ethylimidazole;
4(5)-[2-(4-fluorophenyl)-2-phenyl]ethylimidazole;
4(5)-[2-(2-fluorophenyl)-2-(4'-fluorophenyl)]ethylimidazole;
4(5)-[2-(4-methoxyphenyl)-2-phenyl]ethylimidazole;
4(5)-[(2,2-diphenyl-1-n.propyl)ethenyl]imidazole;
4(5)-[2-(1,1-diphenyl-pentyl]imidazole;
4(5)-[2-(1,1-diphenyl-2-methoxy)pentyl]imidazole;
4(5)-[(2,2-diphenylethyl)-2-methyl]imidazole;
4(5)-[(2,2-diphenylethyl)-5(4)-methyl]imidazole;
4(5)-[2-(2-fluorophenyl)-2-(6'-fluorophenyl)]ethylimidazole;
4(5)-[2-(2-fluorophenyl)-2-phenyl]ethylimidazole;
4(5)-[2-(4-biphenyl)-2-phenyl]ethylimidazole;

4(5)-[1-(2,2-diphenyl)-propyl]imidazole;
4(5)-[2-(2-methylphenyl)-2-(5'-methylphenyl)]e-
thylimidazole;
4(5)-[2-(2-methylphenyl)-2-(4'-methylphenyl)]e-
thylimidazole.

40. A therapeutic method for treating depression in an individual when such therapy is indicated, comprising administering to the individual a therapeutically effective amount of a compound of the formula:

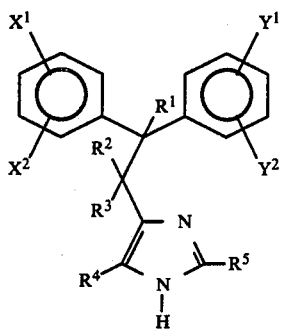

wherein:

$X^1$, $X^2$, $Y^1$, and $Y^2$, which may or may not be identical, are selected from the group consisting of hydrogen, fluoro, chloro, bromo, a linear or branched alkyl radical having from 1 to 3 carbon atoms, a linear or branched alkoxy radical having from 1 to 3 carbon atoms, carboxy, an alkoxy-carbonyl having from 1 to 3 carbon atoms, and phenyl;

$R^1$ is selected from the group consisting of hydrogen, methyl and phenyl;

$R^2$ and $R^3$, which may or may not be identical, are selected from the group consisting of hydrogen, hydroxyl, a linear or branched alkyl having from 1 to 6 carbon atoms, and a linear or branched alkoxy having from 1 to 4 carbon atoms;

$R^1$ and $R^2$ can together form a carbon-carbon double bond;

$R^4$ and $R^5$, which may or may not be identical, are hydrogen or a linear or branched alkyl radical having from 1 to 3 carbon atoms; or a pharmaceutically-acceptable non-toxic salt of addition formed with a pharmaceutically usable acid.

41. The method of claim 40, wherein $X^1$, $X^2$, and $Y^1$ and $Y^2$, which may or may not be identical, are selected from the group consisting of hydrogen, fluoro, chloro, methyl, methoxy and phenyl.

42. The method of claim 41, wherein at least two of the groups $X^1$, $X^2$, $Y^1$ and $Y^2$ are different from hydrogen.

43. The method of claim 41, wherein at least $X^2$ and $Y^1$ are hydrogen.

44. The method of claim 41, wherein $X^1$, $X^2$, $Y^1$ and $Y^2$ are hydrogen.

45. The method of claim 41, wherein one or both of $X^1$ and $Y^1$ are fluoro.

46. The method of claim 41, wherein $R^1$ is hydrogen or a methyl group and $R^2$ is selected from the group consisting of hydrogen, hydroxyl, methyl and methoxy.

47. The method of claim 40, wherein $R^1$ and $R^2$ together form a carbon-carbon double bond.

48. The method of claim 40, wherein $R^3$ is hydrogen or a linear or branched alkyl group having from 1 to 4 carbon atoms.

49. The method of claim 40, wherein $R^4$ and $R^5$, which may or may not be identical, are hydrogen or methyl.

50. The method of claim 40, wherein $R^1$, $R^2$, $R^4$ and $R^5$ are hydrogen.

51. The method of claim 40, wherein $X^1$, $X^2$, $Y^1$, $Y^2$, $R^1$, $R^4$ and $R^5$ are hydrogen.

52. The method of claim 40, wherein said compound is selected from the group consisting of:
4(5)-(2,2-diphenylethyl)imidazole;
4(5)-[(2,2-diphenyl-1-methyl)ethenyl]imidazole;
4(5)-[2-(3-methylphenyl)-2-phenyl]ethylimidazole;
4(5)-[2-(2-chlorophenyl)-2-phenyl]ethylimidazole;
4(5)-[2-(4-fluorophenyl)-2-phenyl]ethylimidazole;
4(5)-[2-(2-fluorophenyl)-2-(4'-fluorophenyl)]e-
thylimidazole;
4(5)-[2-(4-methoxyphenyl)-2-phenyl]ethylimidazole;
4(5)-[(2,2-diphenyl-1-n.propyl)ethenyl]imidazole;
4(5)-[2-(1,1-diphenyl-pentyl]imidazole;
4(5)-[2-(1,1-diphenyl-2-methoxy)pentyl]imidazole;
4(5)-[(2,2-diphenylethyl)-2-methyl]imidazole;
4(5)-[(2,2-diphenylethyl)-5(4)-methyl]imidazole;
4(5)-[2-(2-fluorophenyl)-2-(6'-fluorophenyl)]e-
thylimidazole;
4(5)-[2-(2-fluorophenyl)-2-phenyl]ethylimidazole;
4(5)-[2-(4-biphenyl)-2-phenyl]ethylimidazole;
4(5)-[1-(2,2-diphenyl)-propyl]imidazole;
4(5)-[2-(2-methylphenyl)-2-(5'-methylphenyl)]e-
thylimidazole;
4(5)-[2-(2-methylphenyl)-2-(4'-methylphenyl)]e-
thylimidazole.

53. A therapeutic method for treating a neural degenerative disease in an individual when such therapy is indicated, comprising administering to the individual a therapeutically effective amount of a compound of the formula:

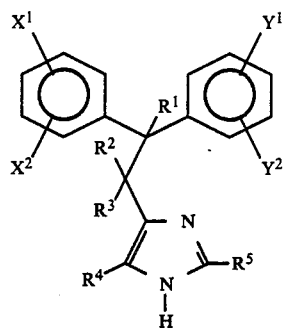

wherein:

$X^1$, $X^2$, $Y^1$, and $Y^2$, which may or may not be identical, are selected from the group consisting of hydrogen, fluoro, chloro, bromo, a linear or branched alkyl radical having from 1 to 3 carbon atoms, a linear or branched alkoxy radical having from 1 to 3 carbon atoms, carboxy, an alkoxy-carbonyl having from 1 to 3 carbon atoms, and phenyl; $R^1$ is selected from the group consisting of hydrogen, methyl and phenyl;

$R^2$ and $R^3$, which may or may not be identical, are selected from the group consisting of hydrogen, hydroxyl, a linear or branched alkyl having from 1 to 6 carbon atoms, and a linear or branched alkoxy having from 1 to 4 carbon atoms;

$R^1$ and $R^2$ can together form a carbon-carbon double bond;

R⁴ and R⁵, which may or may not be identical, are hydrogen or a linear or branched alkyl radical having from 1 to 3 carbon atoms; or a pharmaceutically-acceptable non-toxic salt of addition formed with a pharmaceutically usable acid.

54. The method of claim 53, wherein $X^1$, $X^2$, and $Y^1$ and $Y^2$, which may or may not be identical, are selected from the group consisting of hydrogen, fluoro, chloro, methyl, methoxy and phenyl.

55. The method of claim 54, wherein at least two of the groups $X^1$, $X^2$, $Y^1$ and $Y^2$ are different from hydrogen.

56. The method of claim 54, wherein at least $X^2$ and $Y^1$ are hydrogen.

57. The method of claim 54, wherein $X^1$, $X^2$, $Y^1$ and $Y^2$ are hydrogen.

58. The method of claim 54, wherein one or both of $X^1$ and $Y^1$ are fluoro.

59. The method of claim 54, wherein $R^1$ is hydrogen or a methyl group and $R^2$ is selected from the group consisting of hydrogen, hydroxyl, methyl and methoxy.

60. The method of claim 53, wherein $R^1$ and $R^2$ together form a carbon-carbon double bond.

61. The method of claim 53, wherein $R^3$ is hydrogen or a linear or branched alkyl group having from 1 to 4 carbon atoms.

62. The method of claim 53, wherein $R^4$ and $R^5$, which may or may not be identical, are hydrogen or methyl.

63. The method of claim 53, wherein $R^1$, $R^2$, $R^4$ and $R^5$ are hydrogen.

64. The method of claim 53, wherein $X^1$, $X^2$, $Y^1$, $Y^2$, $R^1$, $R^4$ and $R^5$ are hydrogen.

65. The method of claim 53, wherein said compound is selected from the group consisting of:
4(5)-(2,2-diphenylethyl)imidazole;
4(5)-[2,2-diphenyl-1-methyl)ethenyl]imidazole;
4(5)-[2-(3-methylphenyl)-2-phenyl]ethylimidazole;
4(5)-[2-(2-chlorophenyl)-2-phenyl]ethylimidazole;
4(5)-[2-(4-fluorophenyl)-2-phenyl]ethylimidazole;
4(5)-[2-(2-fluorophenyl)-2-(4'-fluorophenyl)]ethylimidazole;
4(5)-[2-(4-methoxyphenyl)-2-phenyl]ethylimidazole;
4(5)-[(2,2-diphenyl-1-n.propyl)ethenyl]imidazole;
4(5)-[2-(1,1-diphenyl-pentyl]imidazole;
4(5)-[2-(1,1-diphenyl-2-methoxy)pentyl]imidazole;
4(5)-[(2,2-diphenylethyl)-2-methyl]imidazole;
4(5)-[(2,2-diphenylethyl)-5(4)-methyl]imidazole;
4(5)-[2-(2-fluorophenyl)-2-(6'-fluorophenyl)]ethylimidazole;
4(5)-[2-(2-fluorophenyl)-2-phenyl]ethylimidazole;
4(5)-[2-(4-biphenyl)-2-phenyl]ethylimidazole;
4(5)-[1-(2,2-diphenyl)-propyl]imidazole;
4(5)-[2-(2-methylphenyl)-2-(5'-methylphenyl)]ethylimidazole;
4(5)-[2-(2-methylphenyl)-2-(4'-methylphenyl)]ethylimidazole.

66. A therapeutic method for treating metabolic disorders in an individual when such therapy is indicated, comprising administering to the individual a therapeutically effective amount of a compound of the formula:

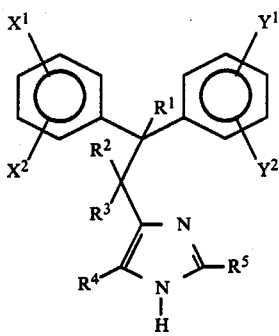

wherein:

$X^1$, $X^2$, $Y^1$, and $Y^2$, which may or may not be identical, are selected from the group consisting of hydrogen, fluoro, chloro, bromo, a linear or branched alkyl radical having from 1 to 3 carbon atoms, a linear or branched alkoxy radical having from 1 to 3 carbon atoms, carboxy, an alkoxy-carbonyl having from 1 to 3 carbon atoms, and phenyl;

$R^1$ is selected from the group consisting of hydrogen, methyl and phenyl;

$R^2$ and $R^3$, which may or may not be identical, are selected from the group consisting of hydrogen, hydroxyl, a linear or branched alkyl having from 1 to 6 carbon atoms, and a linear or branched alkoxy having from 1 to 4 carbon atoms;

$R^1$ and $R^2$ can together form a carbon-carbon double bond;

$R^4$ and $R^5$, which may or may not be identical, are hydrogen or a linear or branched alkyl radical having from 1 to 3 carbon atoms; or a pharmaceutically-acceptable non-toxic salt of addition formed with a pharmaceutically usable acid.

67. The method of claim 66, wherein $X^1$, $X^2$, and $Y^1$ and $Y^2$, which may or may not be identical, are selected from the group consisting of hydrogen, fluoro, chloro, methyl, methoxy and phenyl.

68. The method of claim 67, wherein at least two of the groups $X^1$, $X^2$, $Y^1$ and $Y^2$ are different from hydrogen.

69. The method of claim 67, wherein at least $X^2$ and $Y^1$ are hydrogen.

70. The method of claim 67, wherein $X^1$, $X^2$, $Y^1$ and $Y^2$ are hydrogen.

71. The method of claim 67, wherein one or both of $X^1$ and $Y^1$ are fluoro.

72. The method of claim 67, wherein $R^1$ is hydrogen or a methyl group and $R^2$ is selected from the group consisting of hydrogen, hydroxyl, methyl and methoxy.

73. The method of claim 66, wherein $R^1$ and $R^2$ together form a carbon-carbon double bond.

74. The method of claim 66, wherein $R^3$ is hydrogen or a linear or branched alkyl group having from 1 to 4 carbon atoms.

75. The method of claim 66, wherein $R^4$ and $R^5$, which may or may not be identical, are hydrogen or methyl.

76. The method of claim 66, wherein $R^1$, $R^2$, $R^4$ and $R^5$ are hydrogen.

77. The method of claim 66, wherein $X^1$, $X^2$, $Y^1$, $Y^2$, $R^1$, $R^4$ and $R^5$ are hydrogen.

78. The method of claim 66, wherein said compound is selected from the group consisting of:
4(5)-(2,2-diphenylethyl)imidazole;

4(5)-[(2,2-diphenyl-1-methyl)ethenyl]imidazole;
4(5)-[2-(3-methylphenyl)-2-phenyl]ethylimidazole;
4(5)-[2-(2-chlorophenyl)-2-phenyl]ethylimidazole;
4(5)-[2-(4-fluorophenyl)-2-phenyl]ethylimidazole;
4(5)-[2-(2-fluorophenyl)-2-(4'-fluorophenyl)]ethylimidazole;
4(5)-[2-(4-methoxyphenyl)-2-phenyl]ethylimidazole;
4(5)-[(2,2-diphenyl-1-n.propyl)ethenyl]imidazole;
4(5)-[2-(1,1-diphenyl-pentyl]imidazole;
4(5)-[2-(1,1-diphenyl-2-methoxy)pentyl]imidazole;
4(5)-[2,2-diphenylethyl)-2-methyl]imidazole;
4(5)-[(2,2-diphenylethyl)-5(4)-methyl]imidazole;
4(5)-[2-(2-fluorophenyl)-2-(6'-fluorophenyl)]ethylimidazole;
4(5)-[2-(2-fluorophenyl)-2-phenyl]ethylimidazole;
4(5)-[2-(4-biphenyl)-2-phenyl]ethylimidazole;
4(5)-[1-(2,2-diphenyl)-propyl]imidazole;
4(5)-[2-(2-methylphenyl)-2-(5'-methylphenyl)]ethylimidazole;
4(5)-[2-(2-methylphenyl)-2-(4'-methylphenyl)]ethylimidazole.

* * * * *